US012640266B2

(12) United States Patent
Wu et al.

(10) Patent No.: US 12,640,266 B2
(45) Date of Patent: May 26, 2026

(54) DIAGNOSTIC TOOL FOR ANALYZING RESULTS OF FLOW MEDIATED DILATION

(71) Applicants: Villanova University, Villanova, PA (US); The Trustees of the University of Pennsylvania, Philadelphia, PA (US)

(72) Inventors: Qianhong Wu, Malvern, PA (US); Sridhar Santhanam, Collegeville, PA (US); Bchara Sidnawi, Villanova, PA (US); Chandra M. Sehgal, Wayne, PA (US)

(73) Assignee: Villanova University, Villanova, PA (US)

( * ) Notice: Subject to any disclaimer, the term of this patent is extended or adjusted under 35 U.S.C. 154(b) by 758 days.

(21) Appl. No.: 17/530,805

(22) Filed: Nov. 19, 2021

(65) Prior Publication Data

US 2022/0165420 A1 May 26, 2022

Related U.S. Application Data

(60) Provisional application No. 63/116,420, filed on Nov. 20, 2020.

(51) Int. Cl.
*G16H 50/20* (2018.01)
*A61B 5/0285* (2006.01)
(Continued)

(52) U.S. Cl.
CPC ........... *G16H 50/20* (2018.01); *A61B 5/0285* (2013.01); *G06T 7/0012* (2013.01); *G16H 30/20* (2018.01);
(Continued)

(58) Field of Classification Search
CPC .......... G16H 50/20; G16H 30/20; A61B 5/02; A61B 5/0285; A61B 8/0891;
(Continued)

(56) References Cited

U.S. PATENT DOCUMENTS 10,292,597 B2 * 5/2019 Maltz .................. A61B 8/5223
10,485,429 B2 * 11/2019 Lenehan ................. A61B 8/06
(Continued)

OTHER PUBLICATIONS

Zieliński, B., Dróżdż, A., Frołow, M. Fully-Automatic Method for Assessment of Flow-Mediated Dilation. Sep. 10, 2016. Springer, Cham. Computer Vision and Graphics. ICCVG 2016. Lecture Notes in Computer Science( ), vol. 9972. pp 439-450. https://doi.org/10 (Year: 2016).*

(Continued)

*Primary Examiner* — Devin B Henson
*Assistant Examiner* — Molly Halprin
(74) *Attorney, Agent, or Firm* — Duane Morris LLP

(57) ABSTRACT

A diagnostic tool includes a communications interface, a memory storing instructions, and at least one processor coupled to the communications interface and to the memory. The at least one processor is configured to execute the instructions to perform operations including: receiving measurement data of a response to a flow-mediated dilation (FMD) test; determining a value for an FMD parameter based on the received measurement data; establishing a diagnostic threshold based on patient medical information; determining a diagnostic result of the FMD test by comparing the FMD parameter value to the diagnostic threshold; and providing the diagnostic result of the FMD test through a digital interface of the diagnostic apparatus.

20 Claims, 28 Drawing Sheets

(51) Int. Cl.
    *G06T 7/00* (2017.01)
    *G16H 30/20* (2018.01)
(52) U.S. Cl.
    CPC .............. *G06T 2207/10132* (2013.01); *G06T 2207/20084* (2013.01); *G06T 2207/30104* (2013.01)
(58) Field of Classification Search
    CPC ................ A61B 8/5223; G06T 7/0012; G06T 2207/10132; G06T 2207/20084; G06T 2207/30104; G06T 2207/30101
    USPC ........................................................ 600/485
    See application file for complete search history.

(56) References Cited

U.S. PATENT DOCUMENTS

| | | | | |
|---|---|---|---|---|
| 10,568,582 | B2 * | 2/2020 | Lenehan ............ | A61B 5/02007 |
| 10,758,130 | B2 * | 9/2020 | Mullin ............... | A61B 5/02255 |
| 2010/0081941 | A1 * | 4/2010 | Naghavi ............ | A61B 5/02007 |
| | | | | 600/481 |
| 2014/0066738 | A1 * | 3/2014 | Kassab .................. | A61B 5/053 |
| | | | | 600/374 |
| 2016/0029972 | A1 * | 2/2016 | Lenehan ............ | A61B 5/02007 |
| | | | | 600/479 |
| 2019/0159728 | A1 * | 5/2019 | Pritchard ............. | A61B 5/6812 |

OTHER PUBLICATIONS

Wang H, et al. "Effects of size and elasticity on the relation between flow velocity and wall shear stress . . . A lattice Boltzmann-based computer simulation study." PLoS One 15(1): e0227770. https:// doi.org/10.1371/journal.pone.0227770 (Year: 2020).*

Alaraj, A., et al., 2015. Changes in wall shear stress of cerebral arteriovenous malformation feeder arteries after embolization and surgery. Stroke 46 (5), 1216-1220. https://doi.org/10.1161/strokeaha. 115.008836.

Birk, Gurpreet K., et al., 2012. Brachial artery adaptation to lower limb exercise training: role of shear stress. J. Appl. Physiol. 112 (10), 1653-1658. https://doi.org/10.1152/ japplphysiol.01489.2011. American Physiological Society.

Capell, Brian C., et al., 2007. Mechanisms of cardiovascular disease in accelerated aging syndromes. Circ. Res. 101 (1), 13-26. https:// doi.org/10.1161/ circresaha.107.153692. Ovid Technologies (Wolters Kluwer Health).

Carter, Howard H., et al., 2016. Evidence for shear stress-mediated dilation of the internal carotid artery in humans. Hypertension 68 (5), 1217-1224. https://doi.org/ 10.1161/hypertensionaha.116. 07698. Ovid Technologies (Wolters Kluwer Health).

Carter, Howard H., et al., 2017. Differential impact of water immersion on arterial blood flow and shear stress in the carotid and brachial arteries of humans. Physiol. Rep. 5, 10. https://doi.org/10. 14814/phy2.13285.

Celermajer, D.S., et al., 1993. Cigarette smoking is associated with dose-related and potentially reversible impairment of endothelium-dependent dilation in healthy young adults. Circulation 88 (5), 2149-2155. https://doi.org/10.1161/01.cir.88.5.2149.

Chang, Audrey N., Potter, James D., 2005. Sarcomeric protein mutations in dilated cardiomyopathy. Heart Fail. Rev. 10 (3), 225-235. https://doi.org/10.1007/s10741- 005-5252-6.

Chen, Zhen, et al., 2019. Brachial flow-mediated dilation by continuous monitoring of arterial cross-section with ultrasound imaging. Ultrasound 27 (4), 241-251. https:// doi.org/10.1177/ 1742271x19857770. SAGE Publications.

Cheng, Caroline, et al., 2006. Atherosclerotic lesion size and vulnerability are determined by patterns of fluid shear stress. Circulation 113 (23), 2744-2753. https://doi.org/10.1161/circulationaha. 105.590018.

Chien, Shu, 2007. Mechanotransduction and endothelial cell homeostasis: the wisdom of the cell. Am. J. Physiol. Heart Circ. Physiol. 292 (3) https://doi.org/10.1152/ ajpheart.01047.2006.

Cibis, Merih, et al., 2016. Relation between wall shear stress and carotid artery wall thickening MRI versus CFD. J. Biomech. 49 (5), 735-741. https://doi.org/10.1016/j. jbiomech.2016.02.004. Elsevier BV.

Delmas, Patrick, 2004. Polycystins. Cell 118 (2), 145-148. https:// doi.org/10.1016/j.cell.2004.07.007.

Dong, Cheng, et al., 2005. Melanoma cell extravasation under flow conditions is modulated by leukocytes and endogenously produced interleukin 8. Mol. Cell. BioMech. 2 (3), 145-159.

Farag, Emile S., et al., 2018. Aortic valve stenosis and aortic diameters determine the extent of increased wall shear stress in bicuspid aortic valve disease. J. Magn. Reson. Imag. 48 (2), 522-530. https://doi.org/10.1002/jmri.25956.

Garcia-Cardena, G., et al., 2001. Biomechanical activation of vascular endothelium as A determinant of its functional phenotype. Proc. Natl. Acad. Sci. Unit. States Am. 98 (8), 4478-4485. https:// doi.org/10.1073/pnas.071052598. Proceedings Of The National Academy Of Sciences.

Giantsos-Adams, Kristina M., et al., 2013. Heparan sulfate regrowth profiles under laminar shear flow following enzymatic degradation. Cell. Mol. Bioeng. 6 (2), 160-174. https://doi.org/10.1007/s12195-013-0273-z.

Gouverneur, M., et al., 2006. Vasculoprotective properties of the endothelial glycocalyx: effects of fluid shear stress. J. Intern. Med. 259 (4), 393-400. https://doi.org/ 10.1111/j.1365-2796.2006.01625. x. Wiley.

Hashimoto, M., et al., 1998. The impairment of flow-mediated vasodilatation in obese men with visceral fat accumulation. Int. J. Obes. 22 (5), 477-484. https://doi.org/10.1038/sj.ijo.0800620.

Huang, Sui, Ingber, Donald E., 1999. The structural and mechanical complexity of cell-growth control. Nat. Cell Biol. 1 (5) https://doi. org/10.1038/13043.

Huang, Sui, Ingber, Donald E., 2005. Cell tension, matrix mechanics, and cancer development. Canc. Cell 8 (3), 175-176. https://doi. org/10.1016/j. ccr.2005.08.009. Elsevier BV.

Johnstone, Murray A., 2004. The aqueous outflow system as a mechanical pump. J. Glaucoma 13 (5), 421-438. https://doi.org/10. 1097/01. ijg.0000131757.63542.24.

Kazmierski, M., et al., 2010. Diagnostic value of flow mediated dilatation measurement for coronary artery lesions in men under 45 years of age. J. Cardiol. 17 (3), 288-292.

Burger, et al., 2003. Microgravity and bone cell mechanosensitivity. Adv. Space Res. 32 (8), 1551-1559. https://doi.org/10.1016/s0273-1177(03)90395-4. Elsevier BV.

Knobelsdorff-Brenkenhoff, Von, Florian, et al., 2016. Aortic flow and wall shear stress in aortic stenosis is associated with left ventricular remodeling. J. Cardiovasc. Magn. Reson. 18 (S1) https:// doi.org/10.1186/1532-429x-18-s1-q57.

Koo, Andrew, et al., 2013. Hemodynamic shear stress characteristic of atherosclerosis-resistant regions promotes glycocalyx formation in cultured endothelial cells. Am. J. Physiol. Cell Physiol. 304 (2) https://doi.org/10.1152/ajpcell.00187.2012.

Lammerding, Jan, et al., 2004. Lamin A/C deficiency causes defective nuclear mechanics and mechanotransduction. J. Clin. Invest. 113 (3), 370-378. https://doi.org/ 10.1172/jci19670.

Liang, Shile, Cheng, Dong, 2008. Integrin VLA-4 enhances sialyl-lewisx/A-negative melanoma adhesion to and extravasation through the endothelium under low flow conditions. Am. J. Physiol. Cell Physiol. 295 (3), C701-C707. https://doi.org/ 10.1152/ajpcell.00245. 2008. American Physiological Society.

Liang, Shile, et al., 2008. Hydrodynamic shear rate regulates melanoma-leukocyte aggregation, melanoma adhesion to the endothelium, and subsequent extravasation. Ann. Biomed. Eng. 36 (4), 661-671. https://doi.org/10.1007/s10439-008-9445-8. Springer Nature.

Loth, Francis, et al., 2003. Transitional flow at the venous anastomosis of an arteriovenous graft: potential activation of the ERK1/2 mechanotransduction pathway. J. Biomech. Eng. 125 (1), 49-61. https://doi.org/10.1115/1.1537737. ASME International.

(56) References Cited

OTHER PUBLICATIONS

McCully, Kevin K., 2012. Flow-mediated dilation and cardiovascular disease. J. Appl. Physiol. 112 (12), 1957-1958. https://doi.org/10.1152/japplphysiol.00506.2012. American Physiological Society.

Nauli, Surya M., et al., 2003. Polycystins 1 and 2 mediate mechanosensation in the primary cilium of kidney cells. Nat. Genet. 33 (2), 129-137. https://doi.org/ 10.1038/ng1076.

Ooij, Pim Van, et al., 2014. A methodology to detect abnormal relative wall shear stress on the full surface of the thoracic aorta using four-dimensional flow MRI. Magn. Reson. Med. 73 (3), 1216-1227. https://doi.org/10.1002/mrm.25224.

Paszek, Matthew J., et al., 2005. Tensional homeostasis and the malignant phenotype. Canc. Cell 8 (3), 241-254. https://doi.org/10.1016/j.ccr.2005.08.010.

Pyke, Kyra E., Tschakovsky, Michael E., 2005. The relationship between shear stress and flow-mediated dilatation: Implications for the assessment of endothelial function. J. Physiol. 568 (2), 357-369. https://doi.org/10.1113/physiol.2005.089755.

Restaino, Robert M., et al., 2016. Endothelial dysfunction following prolonged sitting is mediated by A reduction in shear stress. Am. J. Physiol. Heart Circ. Physiol. 310 (5), H648-H653. https://doi.org/10.1152/ajpheart.00943.2015. American Physiological Society.

Abad, et al., AIP Advances 10, 025033 (2020); Simulation strategies for the food and drug administration nozzle using Nek5000. AIP Adv. 10 (2). https://doi. org/10.1063/1.5142703. Accessed Mar. 5, 2020.

Shi, Zhong-Dong, et al., 2011. Heparan sulfate proteoglycans mediate interstitial flow mechanotransduction regulating MMP-13 expression and cell motility via FAK-ERK in 3D collagen. PloS One 6 (1), e15956. https://doi.org/10.1371/journal. pone.0015956. Public Library Of Science (Plos).

Stoner, Lee, et al., 2004. Relationship between blood velocity and conduit artery diameter and the effects of smoking on vascular responsiveness. J. Appl. Physiol. 96 (6), 2139-2145. https://doi.org/10.1152/japplphysiol.01107.2003. American Physiological Society.

Suresh, S., 2007. Biomechanics and biophysics of cancer Cells☆. Acta Biomater. 3 (4), 413-438. https://doi.org/10.1016/j.actbio.2007.04.002.

Tan, J.C.H., 2006. Mechanosensitivity and the eye: cells coping with the pressure. Br. J. Ophthalmol. 90 (3), 383-388. https://doi.org/10.1136/bjo.2005.079905. BMJ.

Verstraeten, Valerie L.R. M., et al., 2008. Increased mechanosensitivity and nuclear stiffness in hutchinson-gilford progeria cells: effects of farnesyltransferase inhibitors. Aging Cell 7 (3), 383-393. https://doi.org/10.1111/.1474-9726.2008.00382.x. Wiley.

Vollrath, Melissa A., et al., 2007. The micromachinery of mechanotransduction in hair cells. Annu. Rev. Neurosci. 30 (1), 339-365. https://doi.org/10.1146/annurev.neuro.29.051605.112917.

Wang, Y., et al., 2006. A model for the role of integrins in flow induced mechanotransduction in osteocytes. J. Biomech. 39, S238. https://doi.org/10.1016/ s0021-9290(06)83892-3. Elsevier BV.

Weinbaum, Sheldon, et al., 2007. The structure and function of the endothelial glycocalyx layer. Annu. Rev. Biomed. Eng. 9 (1), 121-167. https://doi.org/10.1146/ annurev.bioeng.9.060906. 151959. Annual Reviews.

Wolf, Katarina, et al., 2007. Multi-step pericellular proteolysis controls the transition from individual to collective cancer cell invasion. Nat. Cell Biol. 9 (8), 893-904. https://doi.org/10.1038/ncb1616.

Cui, Wei, et al., 2004. Changes in gene expression in response to mechanical strain in human scleral fibroblasts. Exp. Eye Res. 78 (2), 275-284. https://doi.org/10.1016/j. exer.2003.10.007. Elsevier BV.

Heydemann, Ahlke, Mcnally, Elizabeth M., 2007. Consequences of disrupting the dystrophin-sarcoglycan complex in cardiac and skeletal myopathy. Trends Cardiovasc. Med. 17 (2), 55-59. https://doi.org/10.1016/j.tcm.2006.12.002.

Liu, Zhendong, et al., 2016. Low carotid artery wall shear stress is independently associated with brain white-matter hyperintensities and cognitive impairment in older patients. Atherosclerosis 247, 78-86. https://doi.org/10.1016/j.atherosclerosis.2016.02.003. Elsevier BV.

Li, Yi-Shuan, J., et al., 2005. Molecular basis of the effects of shear stress on vascular endothelial cells. J. Biomech. 38 (10), 1949-1971. https://doi.org/10.1016/j.jbiomech.2004.09.030. Elsevier BV.

Martens, Remy J.h., et al., 2013. Sublingual microvascular glycocalyx dimensions in lacunar stroke patients. Cerebrovasc. Dis. 35 (5), 451-454. https://doi.org/10.1159/000348854.

Nakamura, Takamitsu, et al., 2011. Endothelial vasomotor dysfunction in the brachial artery predicts the short-term development of early stage renal dysfunction in patients with coronary artery disease. Int. J. Cardiol. 148 (2), 183-188. https://doi.org/10.1016/j. ijcard.2009.10.054.

Palmer, Bradley M., 2005. Thick filament proteins and performance in human heart failure. Heart Fail. Rev. 10 (3), 187-197. https://doi.org/10.1007/s10741-005-5249-1.

Sarntinoranont, Malisa, et al., 2003. Interstitial stress and fluid pressure within A growing tumor. Ann. Biomed. Eng. 31 (3), 327-335. https://doi.org/10.1114/1.1554923. Springer Nature.

Sidnawi, Bchara, et al., 2019. Characterization of blood velocity in arteries using A combined analytical and Doppler maging approach. Phys. Rev. Fluids 4 (5). https://doi.org/10.1103/physrevfluids.4.053101. American Physical Society (APS).

Timmins, Lucas H., et al., 2014. Focal association between wall shear stress and clinical coronary artery disease progression. Ann. Biomed. Eng. 43 (1), 94-106. https://doi.org/10.1007/s10439-014-1155-9.

* cited by examiner

100

$$s = s_0 * \left(\frac{r_{in}}{r_{in} + u_0(t)}\right)^3$$

DIAGNOSTIC TOOL FOR ANALYZING RESULTS OF FLOW MEDIATED DILATION

CROSS REFERENCE TO RELATED APPLICATIONS

This application claims benefit of U.S. Provisional Patent Application No. 63/116,420 filed Nov. 20, 2020, the entirety of which is incorporated by reference herein.

STATEMENT REGARDING GOVERNMENT SUPPORT

This invention was made with government support under NSF 1511096 awarded by the National Science Foundation. The government has certain rights in the invention.

TECHNICAL FIELD

The present disclosure relates to a diagnostic tool, and, more particularly, to a diagnostic tool for analyzing and using the results of a flow mediated dilation test.

BACKGROUND

One of the indicators of cardiovascular health is the structural integrity of arterial walls. One method for assessing the physical state of the arterial wall is the noninvasive and relatively inexpensive brachial artery Flow-Mediated Dilation (BAFMD) test, in which blood flow through the brachial artery is obstructed temporarily (for about five minutes) using a pressure cuff wrapped around the upper arm, causing the artery to become almost completely closed. The cuff is then suddenly deflated, allowing the flow to rush back in while the dilating artery is monitored until full recovery, using an ultrasound scanner. FMD metrics have been proposed in the past as potential cardiovascular health indicators. Correlations have been found linking abnormal FMD results with many underlying conditions and risk factors directly affecting cardiovascular health. Using high resolution ultrasound imaging, the impairment of BAFMD due to cigarette smoking has been investigated. The conclusions of the said study corroborate the findings of Celermajer, D. S. et al. Cigarette smoking is associated with dose-related and potentially reversible impairment of endothelium-dependent dilation in healthy young adults. Circulation 88, 2149-2155 (1993) reported on the influence that smoking has on the relationship between the arterial diameter and the blood velocity in the brachial artery. BAFMD's predictive power when it comes to the short-term development of early stage renal dysfunction has been established. In a study involving 38 obese men, visceral obesity was linked to BAFMD impairment. In several other studies, monitoring BAFMD has been shown to be instrumental for diagnosing cardiovascular diseases (CVDs) and assessing cardiovascular health. However, there is a significant lack of understanding of the fundamental biophysics governing the FMD process, which prevents it from being an effective and pervasive diagnostic for CVDs. The present disclosure includes a system and device that evaluate the output and results of an FMD process to produce a diagnostic tool that overcomes the previous issues of interpreting an FMD test.

SUMMARY

The summary of the disclosure is given to aid understanding of flow mediated dilation, and more particularly, to a diagnostic tool for analyzing and using the results of a flow mediated dilation test, and not with an intent to limit the disclosure. The present disclosure is directed to a person of ordinary skill in the art. It should be understood that various aspects and features of the disclosure may advantageously be used separately in some instances, or in combination with other aspects and features of the disclosure in other instances. Accordingly, variations and modifications may be made to the systems, devices, and their methods of operation to achieve different effects. Certain aspects of the present disclosure provide a system, method, and non-transitory computer readable medium for flow mediated dilation testing and analysis.

In one or more embodiments, a diagnostic apparatus includes a communications interface, a memory storing instructions, and at least one processor coupled to the communications interface and to the memory. In one or more cases, the at least one processor is configured to execute the instructions to perform operations. In one or more cases, the operations include receiving measurement data of a response to a flow-mediated dilation (FMD) test. In one or more cases, the operations include determining a value for an FMD parameter based on the received measurement data. In one or more cases, the operations include establishing a diagnostic threshold based on patient medical information. In one or more cases, the operations include determining a diagnostic result of the FMD test by comparing the FMD parameter value to the diagnostic threshold. In one or more cases, the operations include providing the diagnostic result of the FMD test through a digital interface of the diagnostic apparatus.

In one or more embodiments, a computer-implemented method includes receiving image data of a patient from a medical diagnostic tool. In one or more cases, the image data corresponds to a response to a flow-mediated dilation (FMD) test. In one or more cases, the computer-implemented method includes deriving measurement data from the received image data. In one or more cases, the computer-implemented method includes determining a value for an FMD parameter based on the measurement data. In one or more cases, the computer-implemented method includes establishing a diagnostic threshold based on patient medical information. In one or more cases, the computer-implemented method includes determining a diagnostic result of the FMD test by comparing the FMD parameter value to the diagnostic threshold. In one or more cases, the computer-implemented method includes providing the diagnostic result of the FMD test through a digital interface of a diagnostic apparatus.

In one or more embodiments, a tangible, non-transitory computer-readable medium storing instructions that, when executed by at least one processor, cause the at least one processor to perform a method. In one or more cases, the method includes receiving image data of a patient from a medical diagnostic tool. In one or more cases, the image data corresponds to a response to a flow-mediated dilation (FMD) test. In one or more cases, the method includes deriving measurement data from the received image data. In one or more cases, the method includes determining a value for an FMD parameter based on the measurement data. In one or more cases, the method includes establishing a diagnostic threshold based on patient medical information. In one or more cases, the method includes determining a diagnostic result of the FMD test by comparing the FMD parameter value to the diagnostic threshold. In one or more cases, the method includes providing the diagnostic result of the FMD test through a digital interface of a diagnostic apparatus.

BRIEF DESCRIPTION OF DRAWINGS

FIGS. 4a-4c illustrate one or more aspects of a BAFMD test, in which FIG. 4(a) illustrates an Ischemic cuff wrapped around the arm for 5 minutes while monitoring the artery, FIG. 4(b) illustrates a snapshot of the monitored artery, and FIG. 4(c) illustrates monitoring the arterial diameter response after deflating the cuff;

Figure 14:
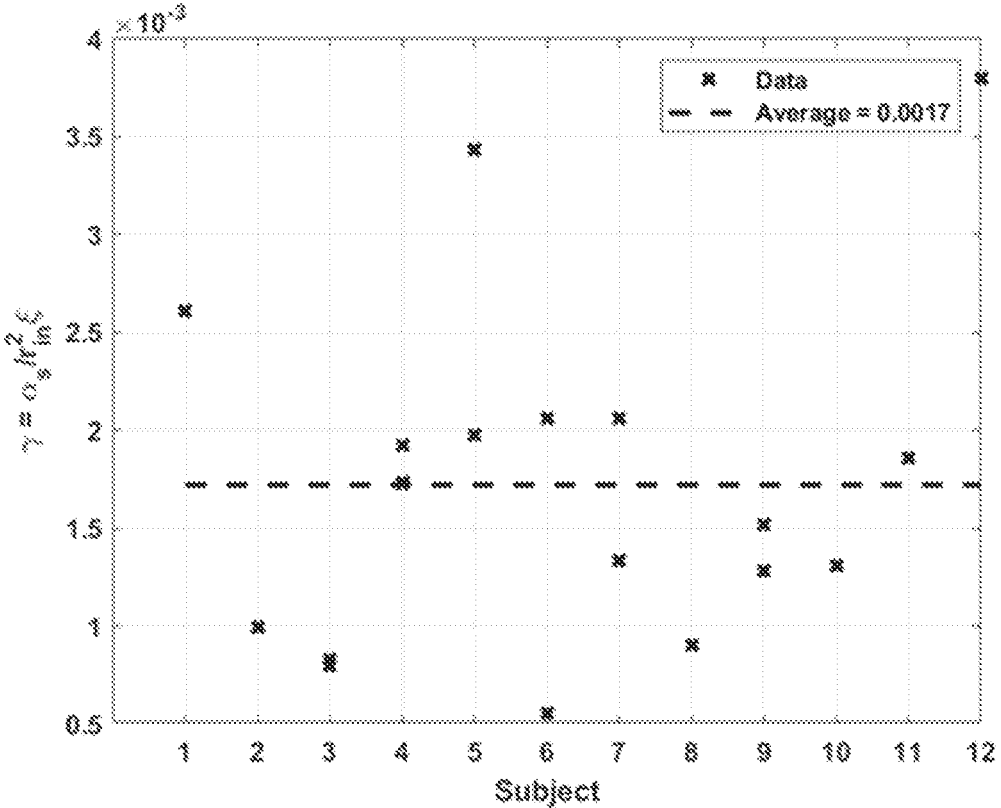
Figure 15:
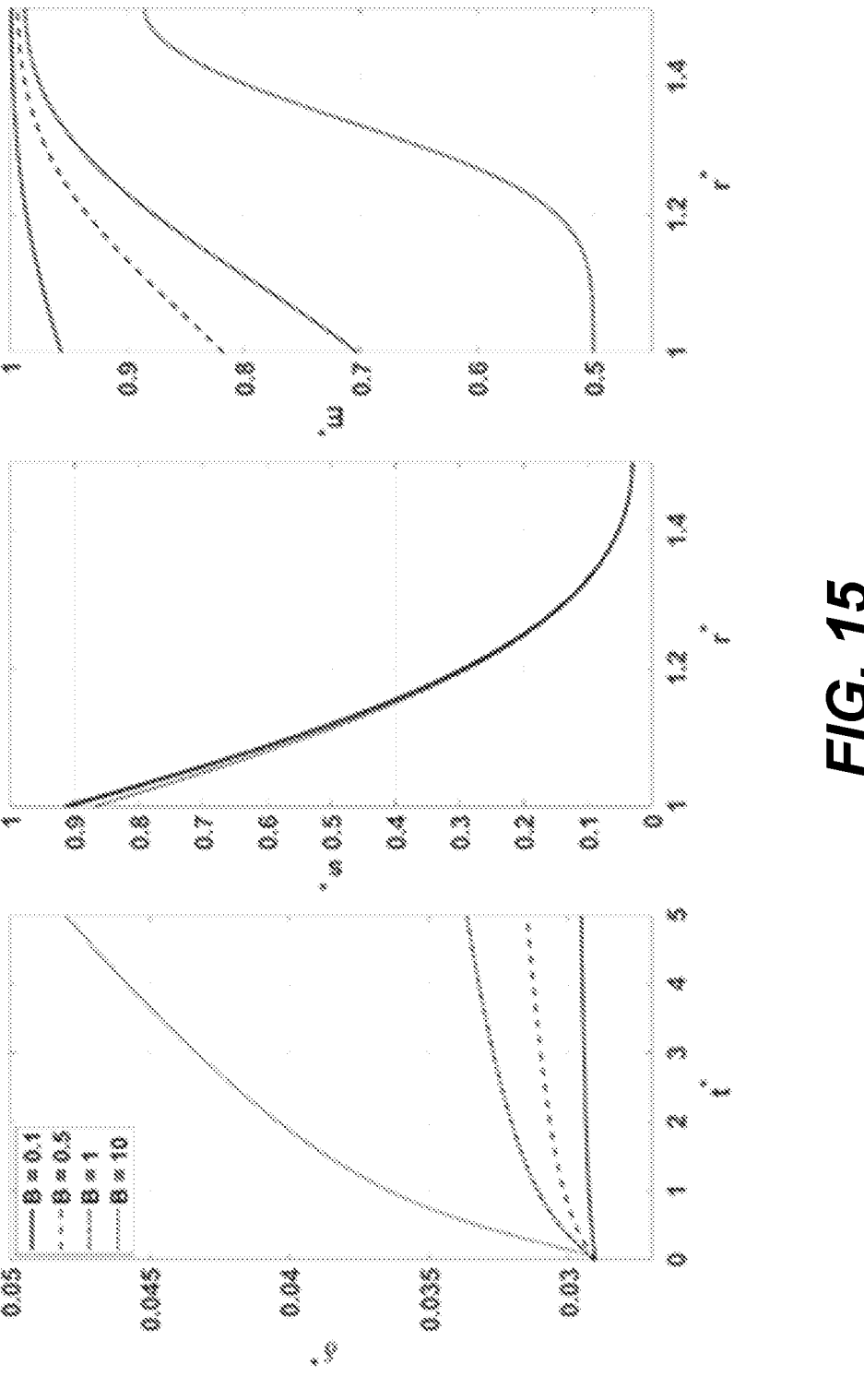
Figure 16:
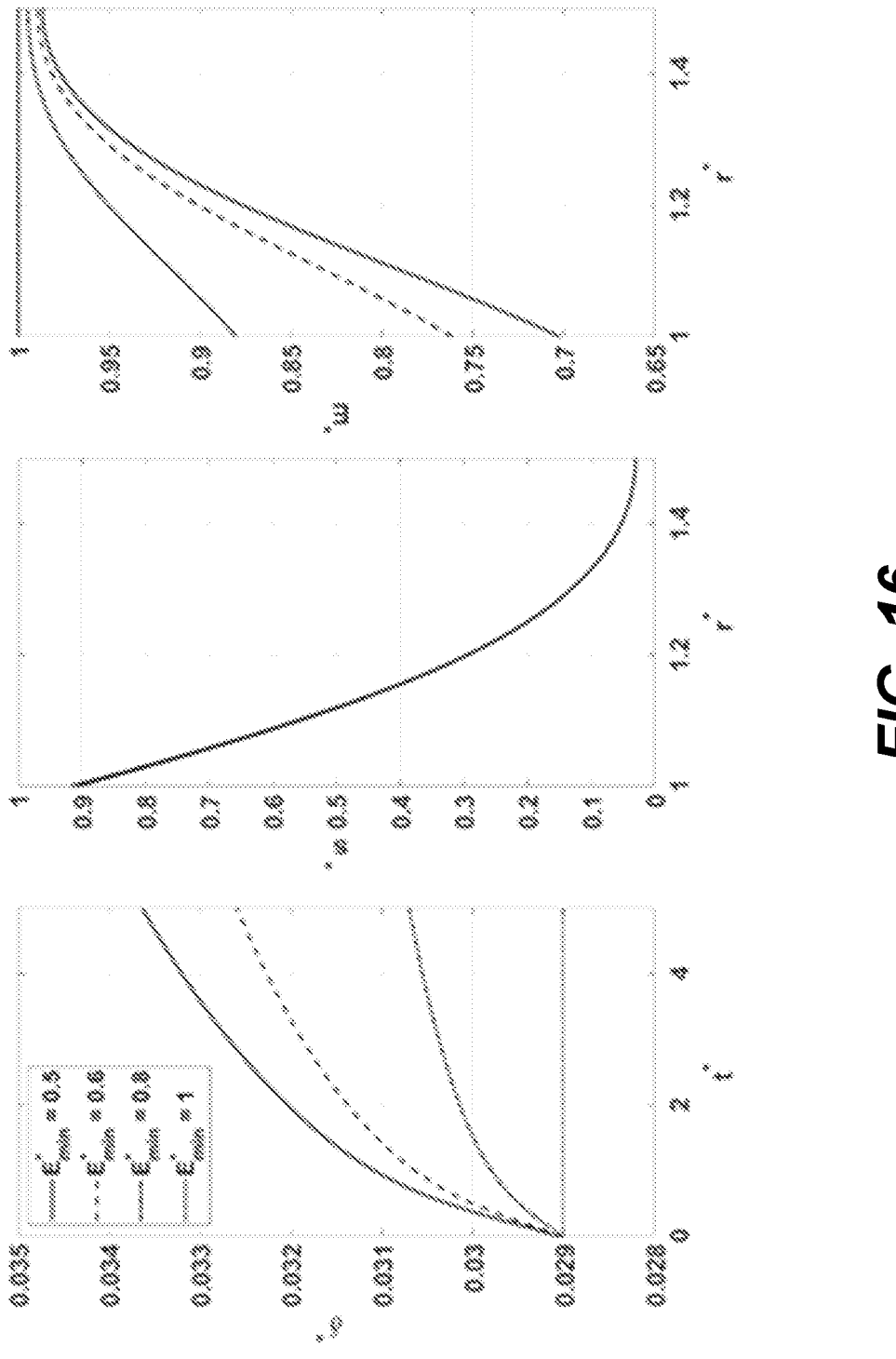
Figure 17:
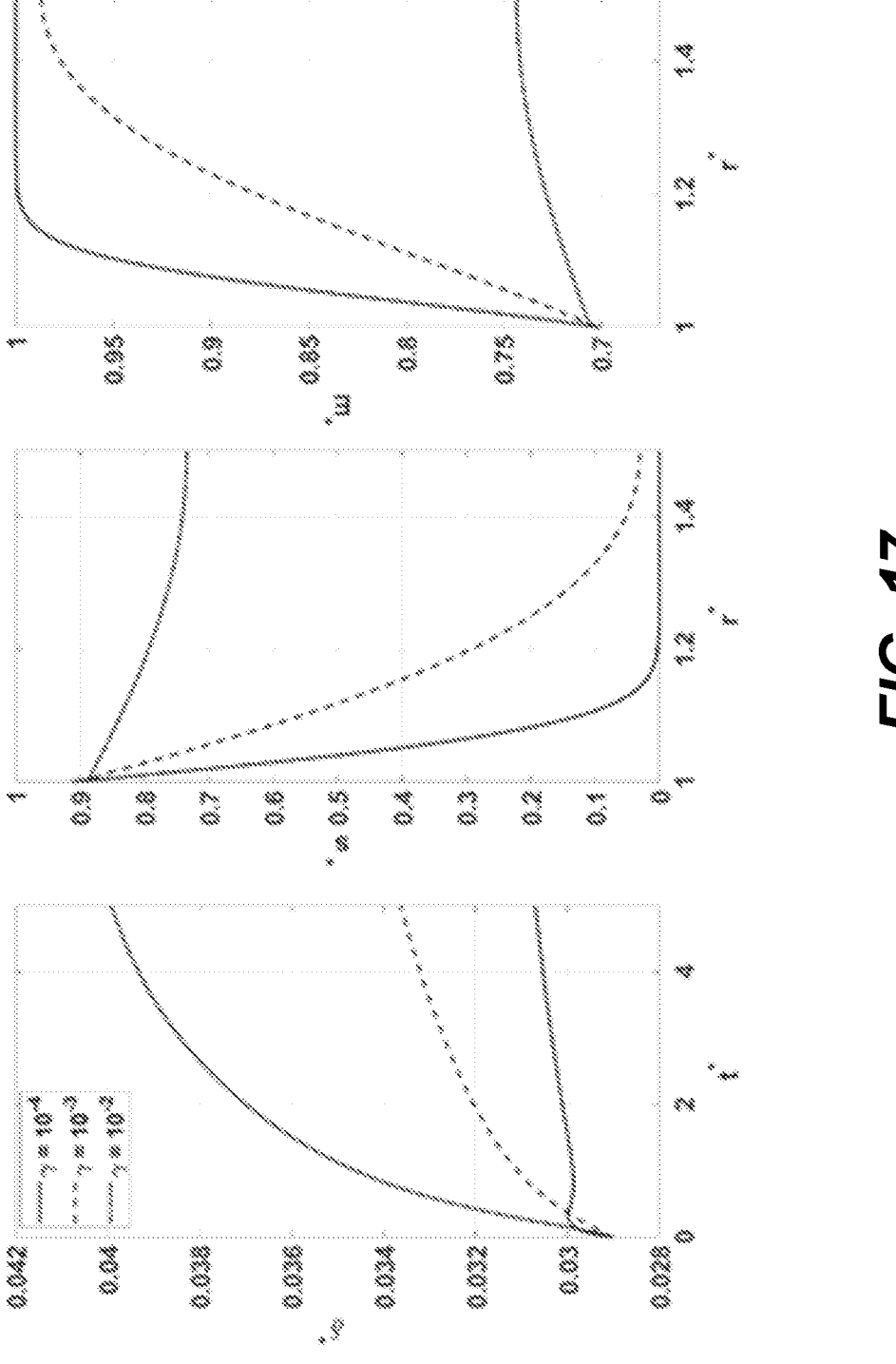
Figure 18A:
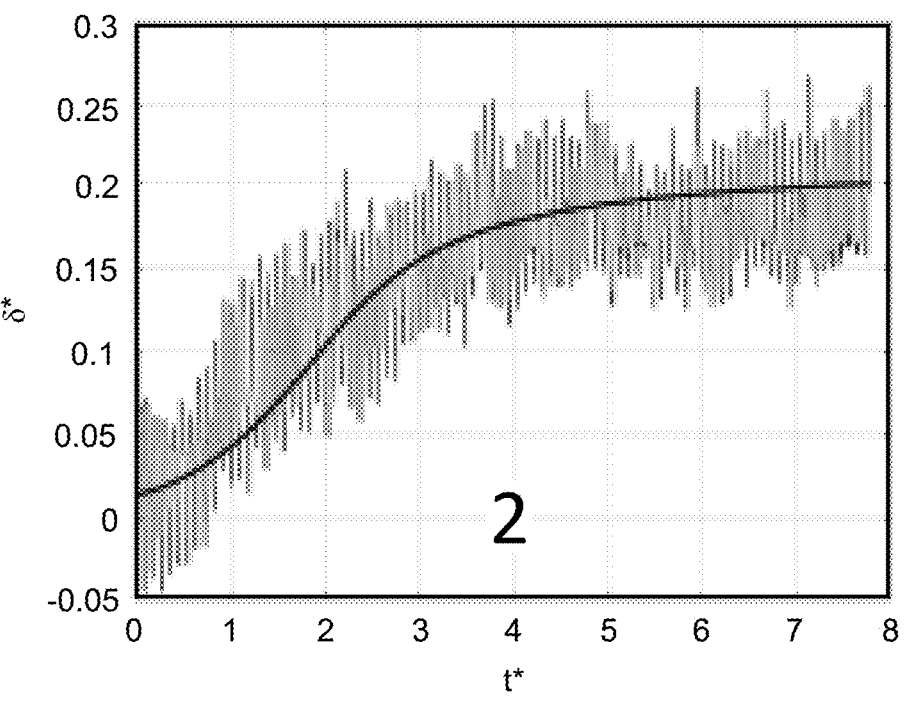
Figure 18B:
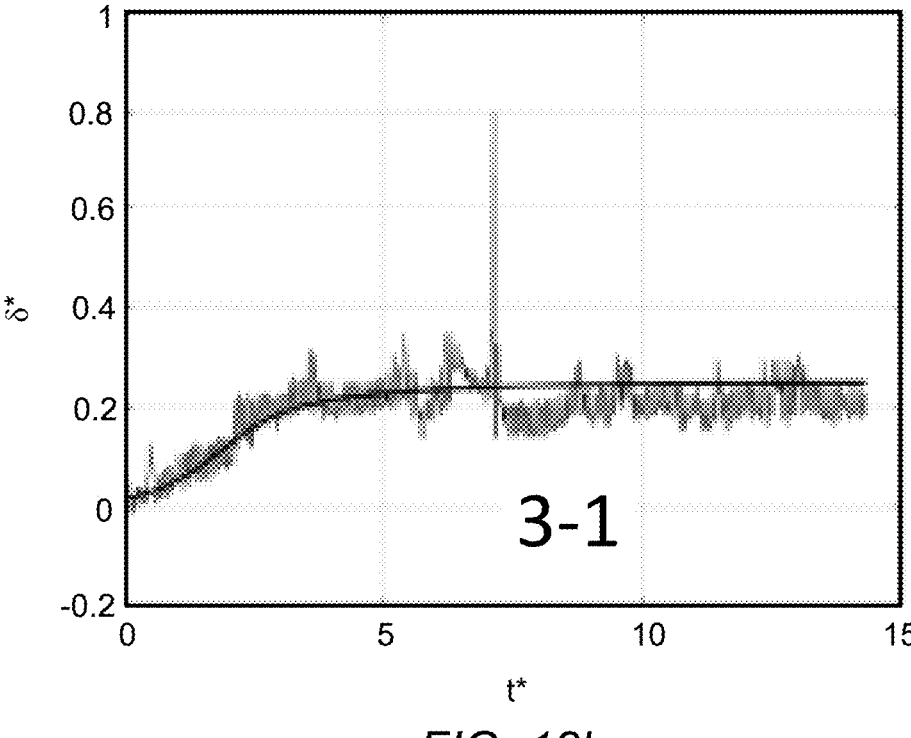
Figure 18C:
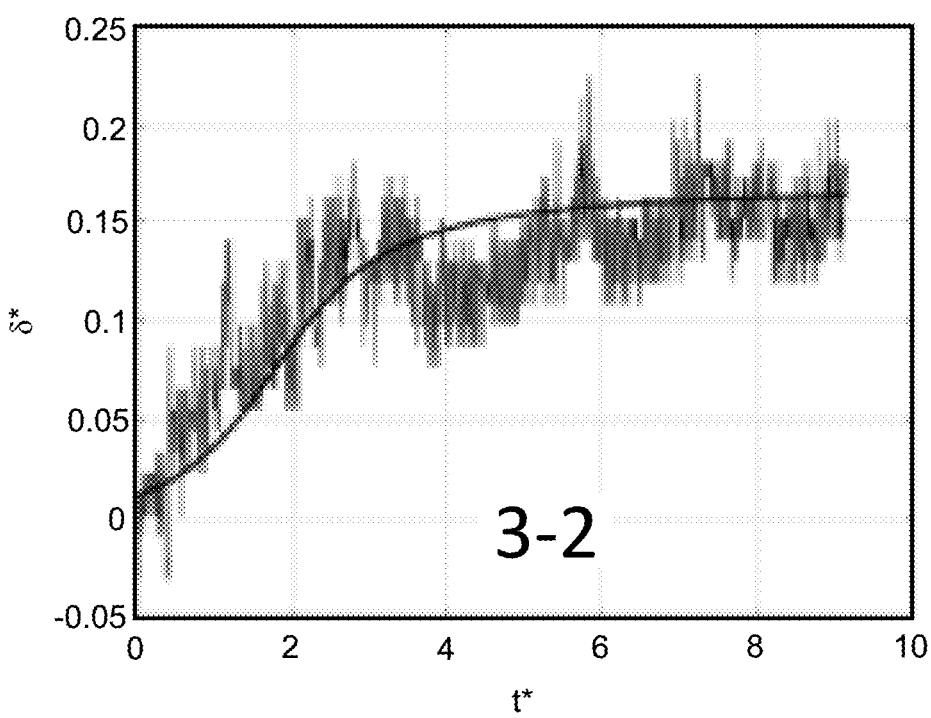
Figure 18D:
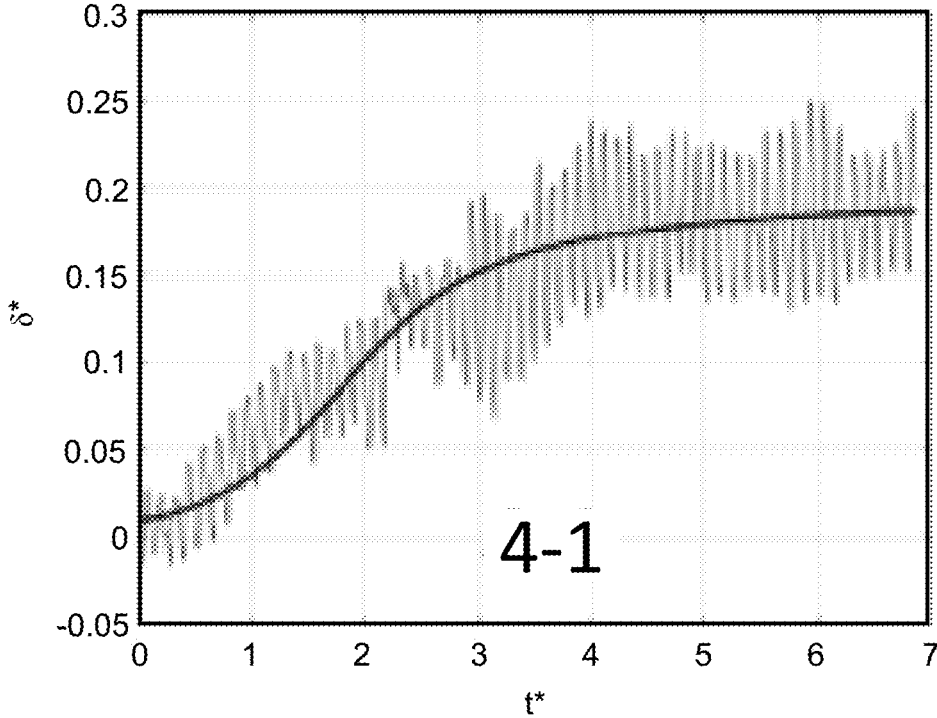
Figure 18E:
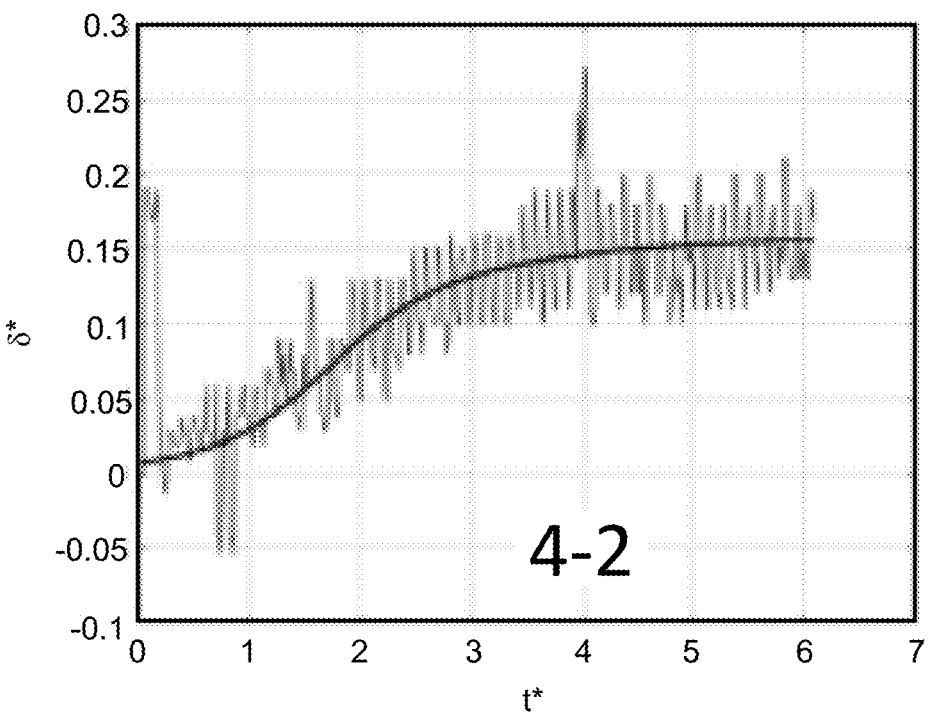
Figure 18F:
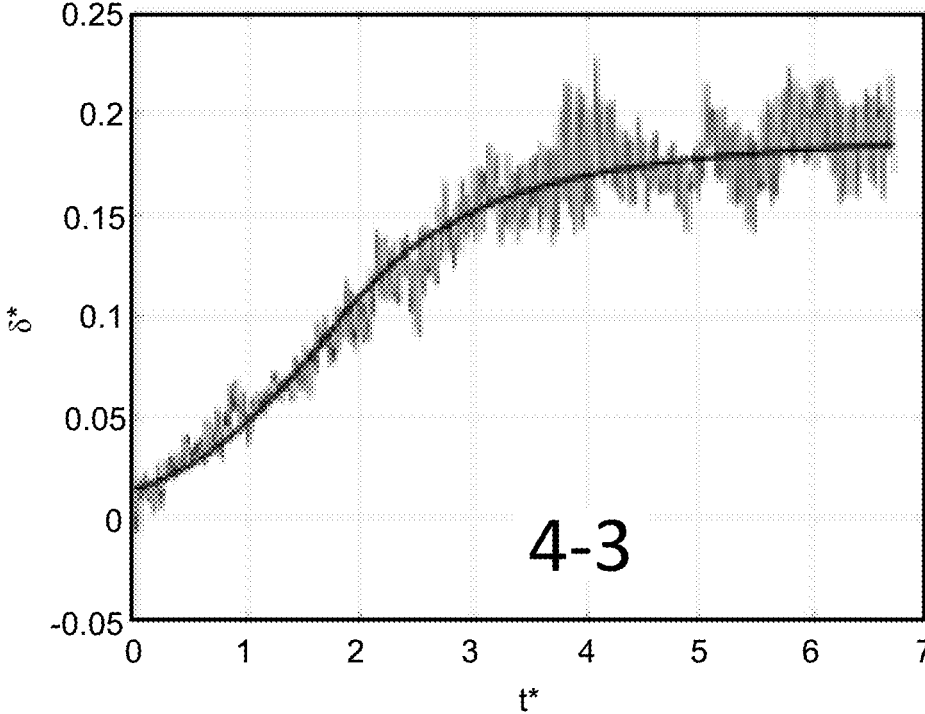
Figure 18G:
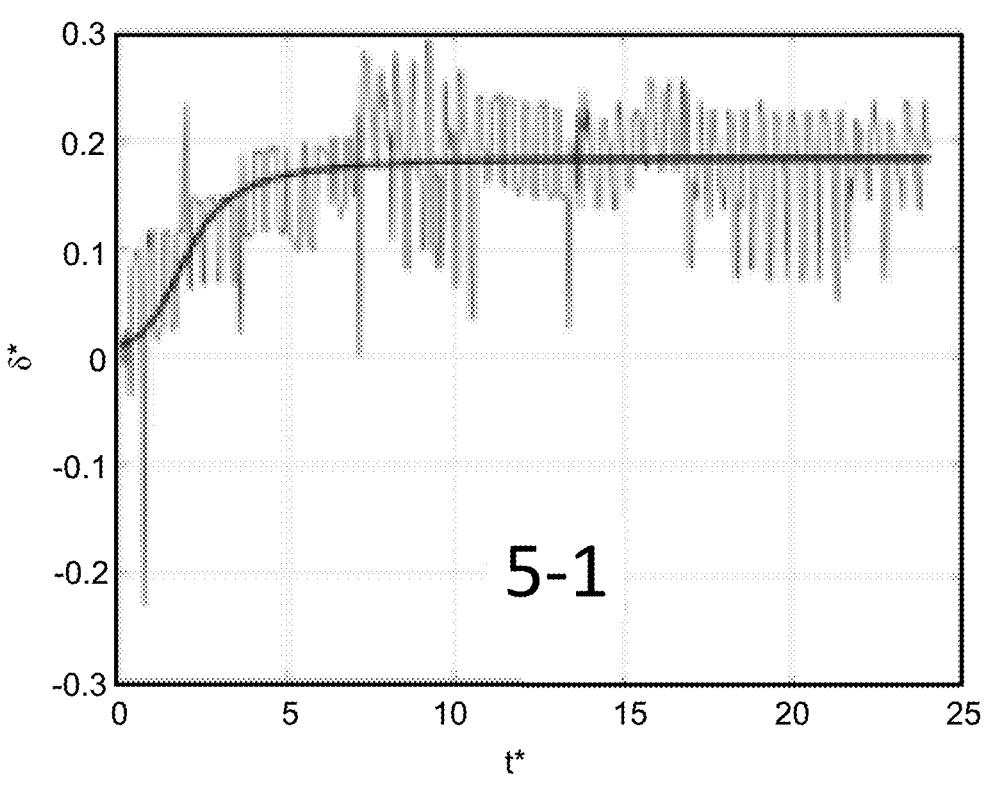
Figure 18H:
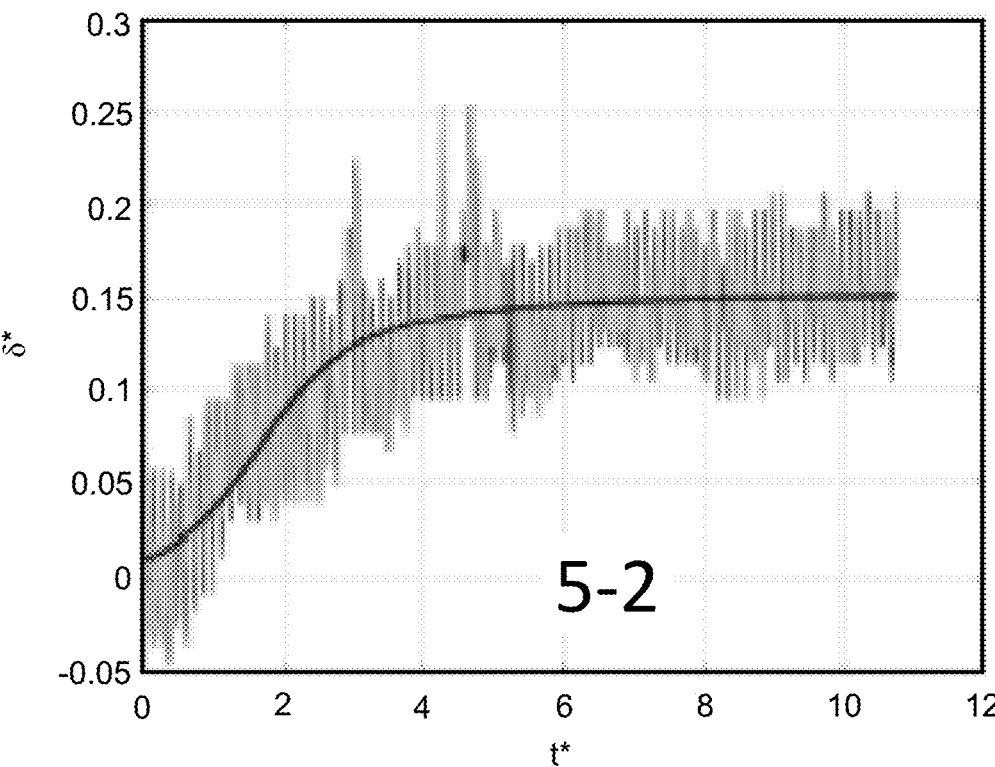
Figures 18I, 18J:
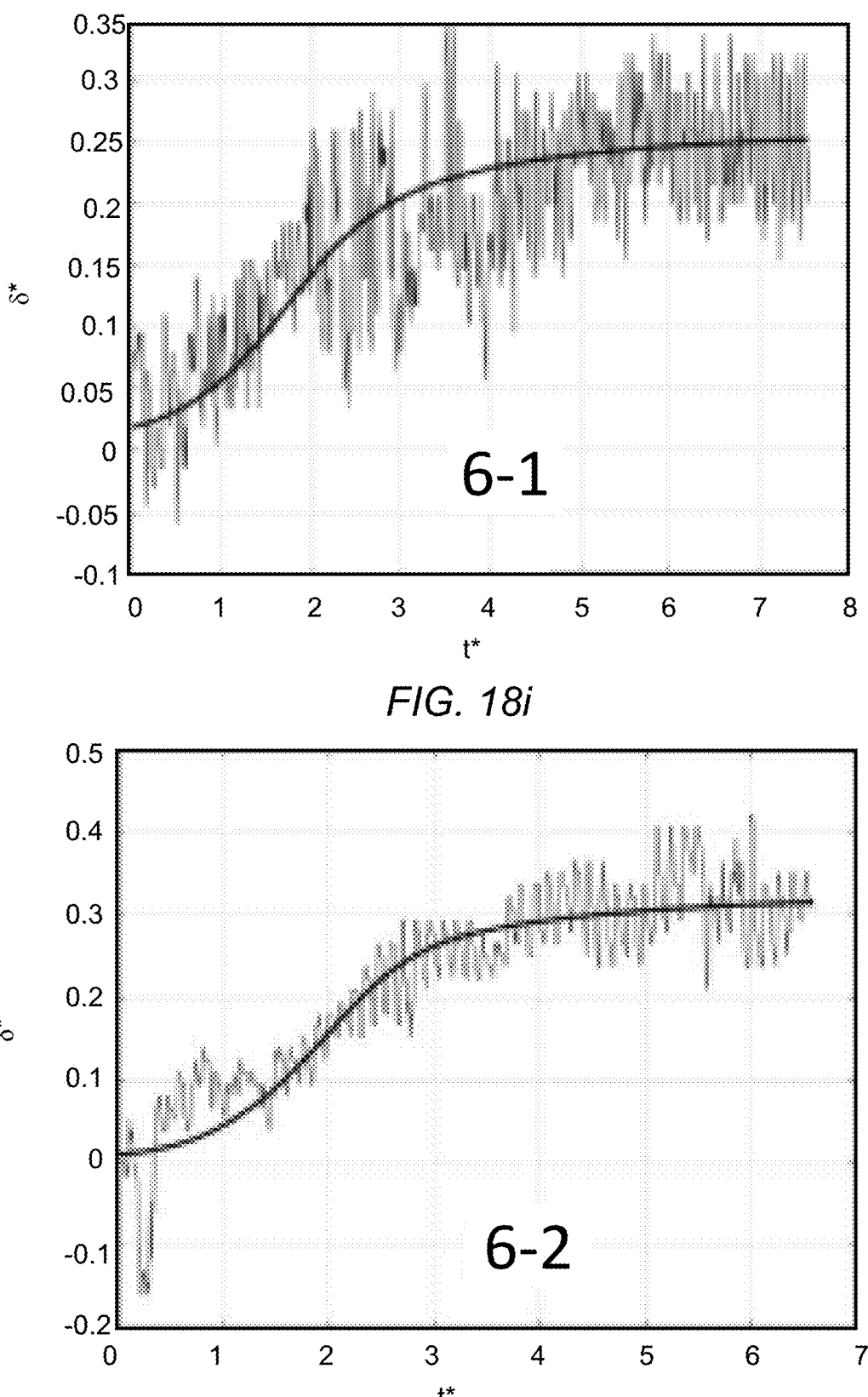
Figure 18K:
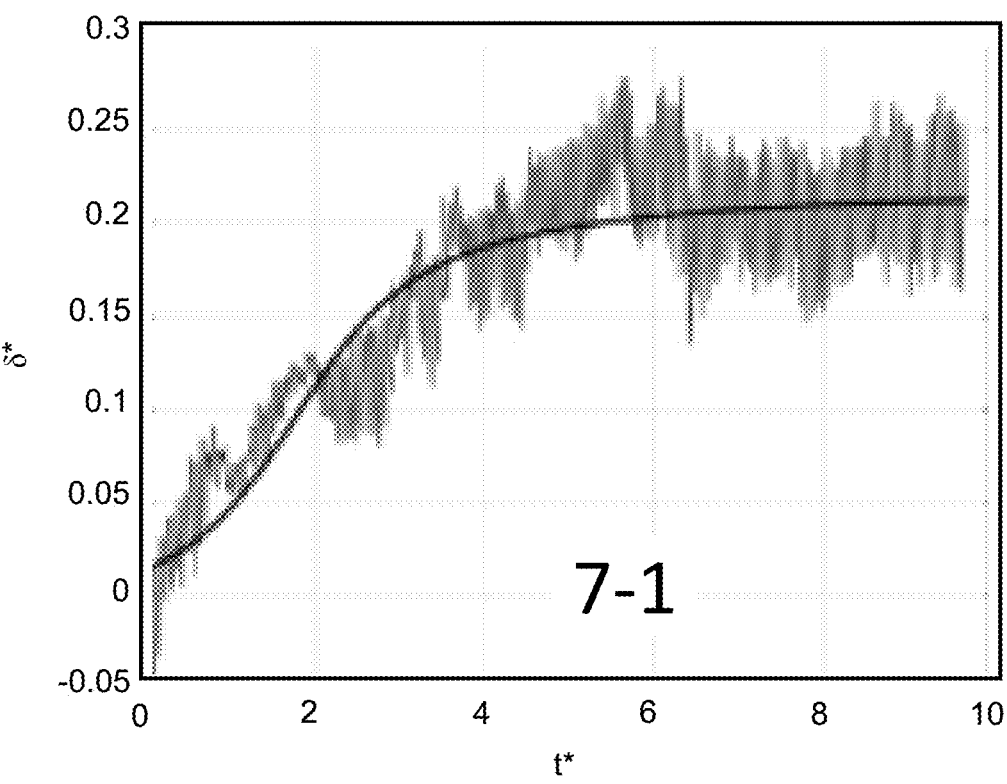
Figure 18L:
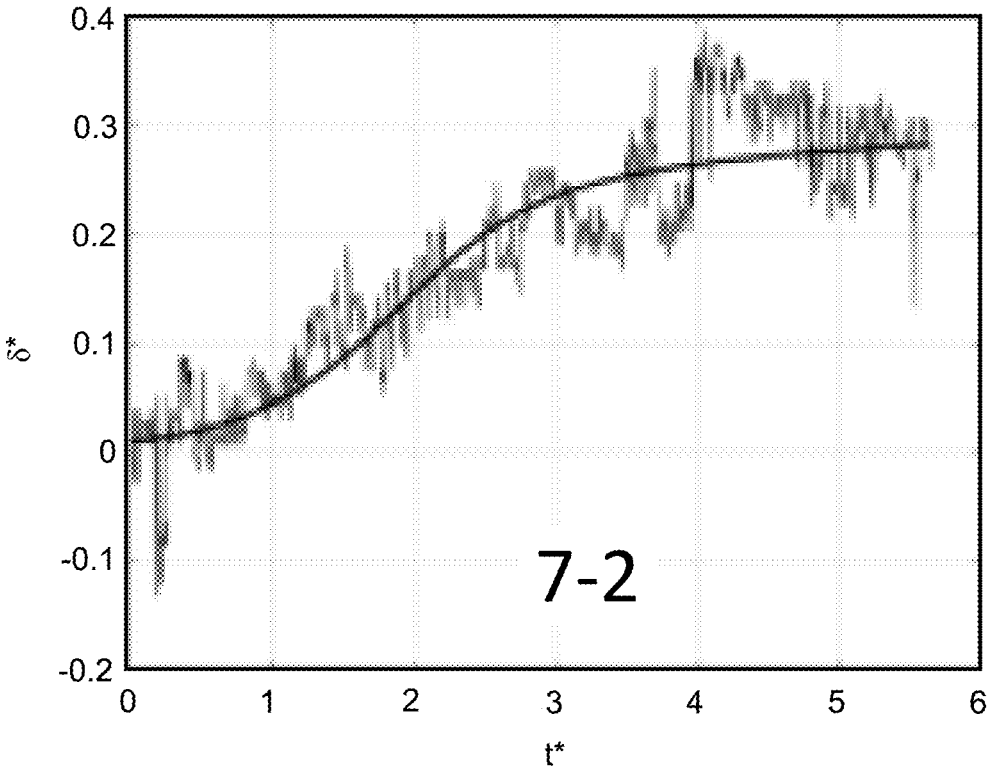
Figure 18M:
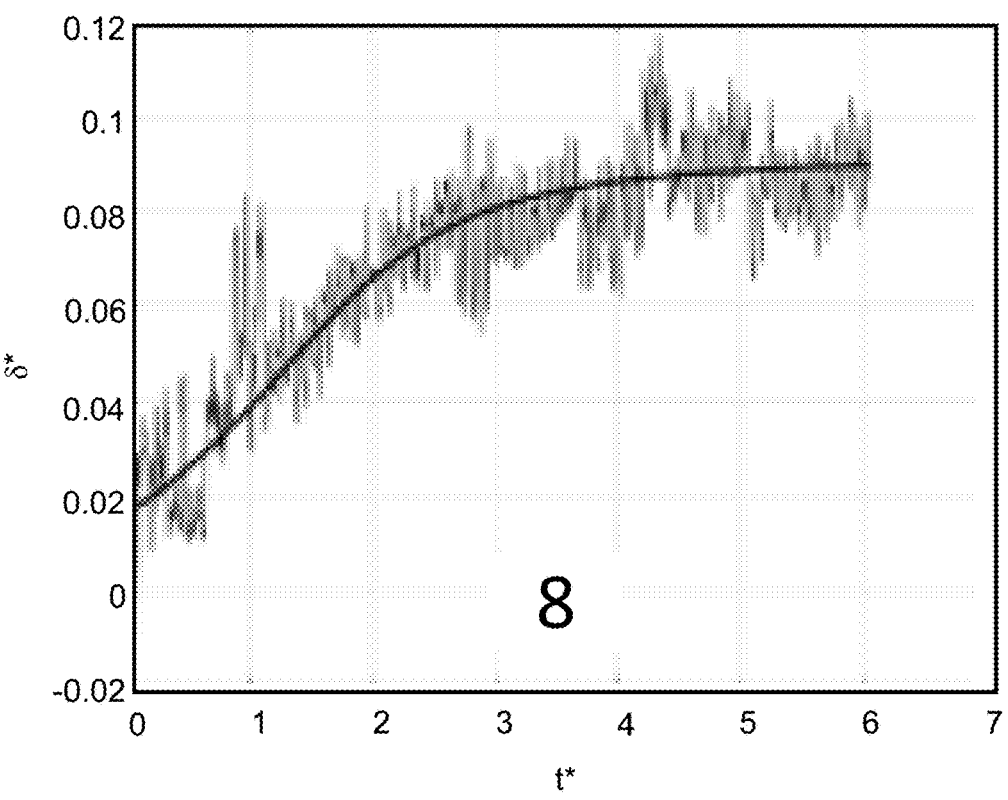
Figure 18N:
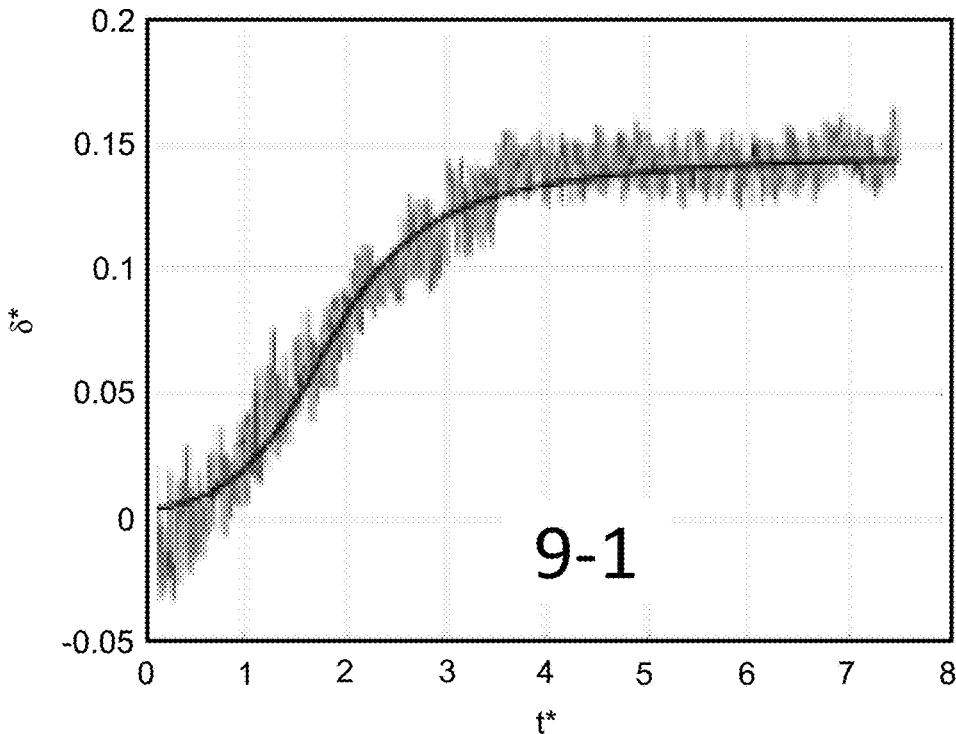
Figure 18O:
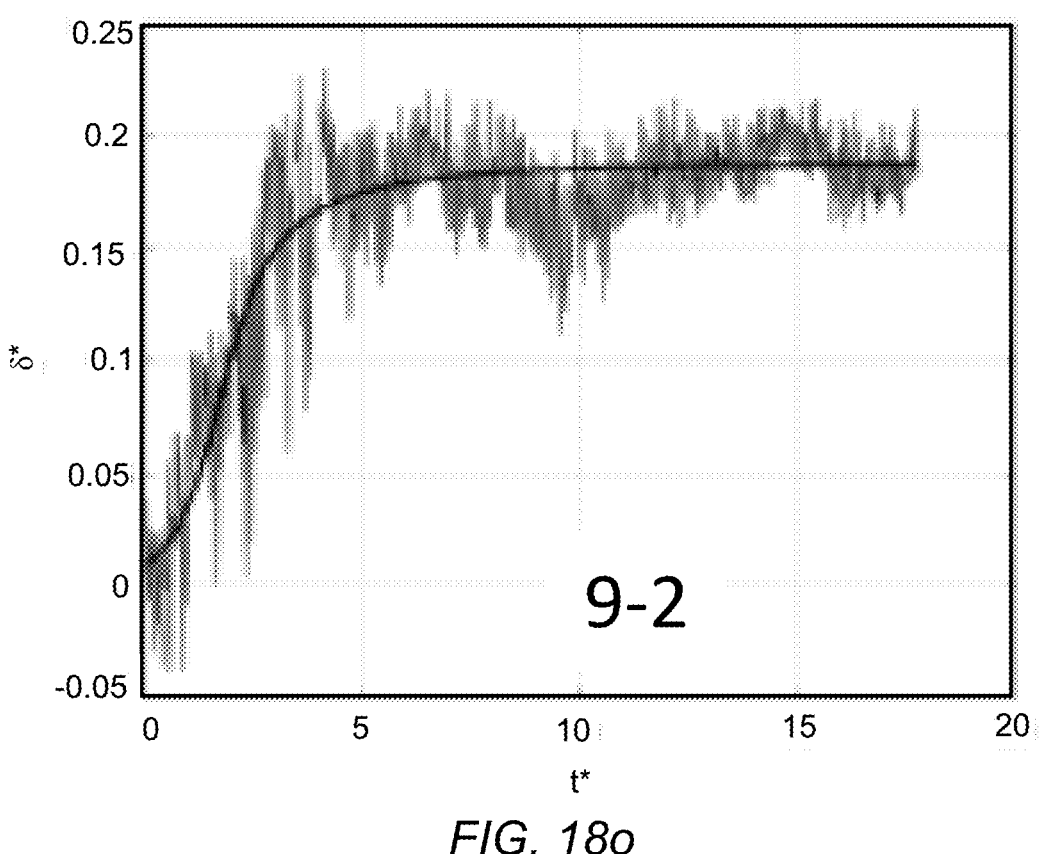
Figure 18P:
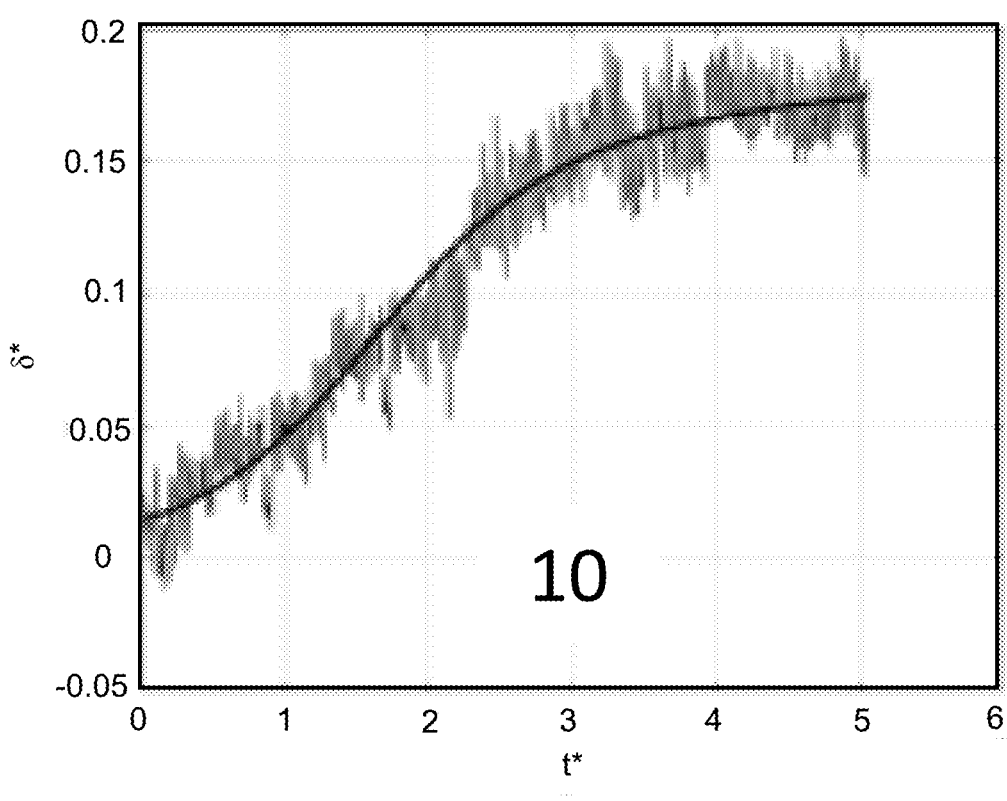
Figure 18Q:
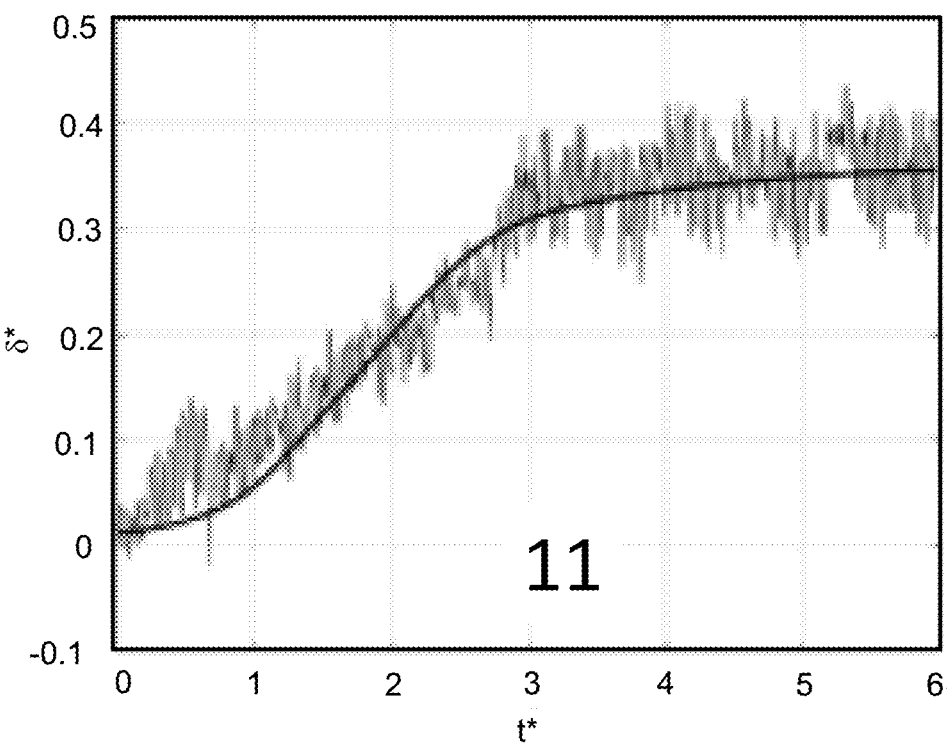
Figure 18R:
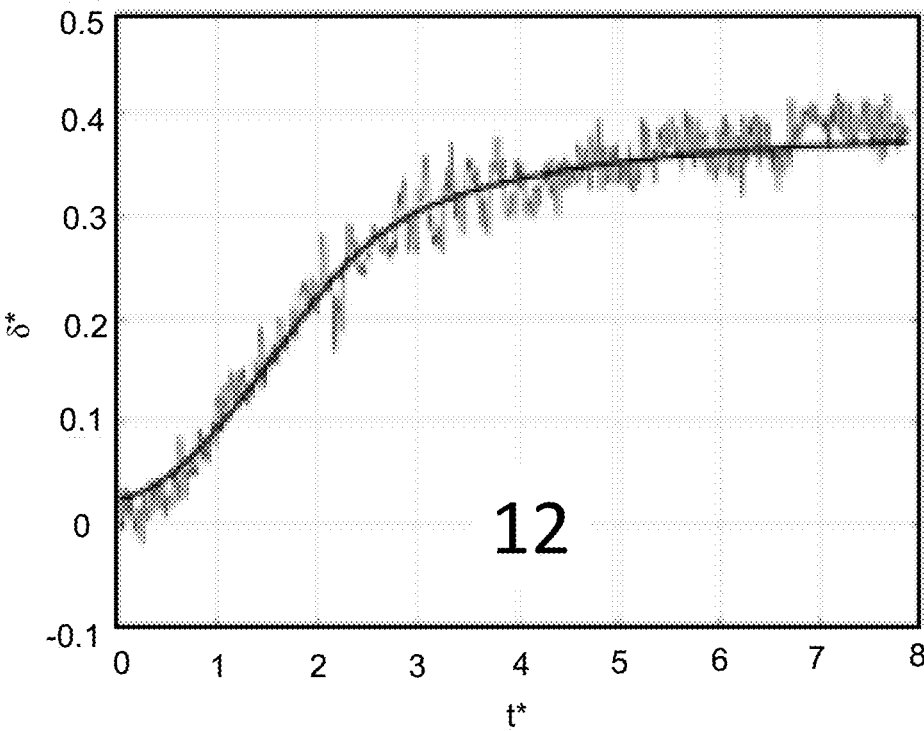

for all subjects;

FIG. 14 is a graph of predicted value of $\gamma$ for all subjects;

FIG. 15 is graphical representations for $\delta^*$, $s^*$, and $E^*$ behavior for different values of B;

FIG. 16 is graphical representations for $\delta^*$, $s^*$, and $E^*$ behavior for different values of $E^*_{min}$;

FIG. 17 is graphical representations for $\delta^*$, $s^*$, and $E^*$ behavior for different values of $\gamma$; and FIGS. 18a-18r are graphs of representative results of fitting the theoretical response to its observed counterpart.

DETAILED DESCRIPTION

The present disclosure relates to a diagnostic tool for processing and analyzing results of a Flow-Mediated Dilation (FMD) test.

Figure 1:
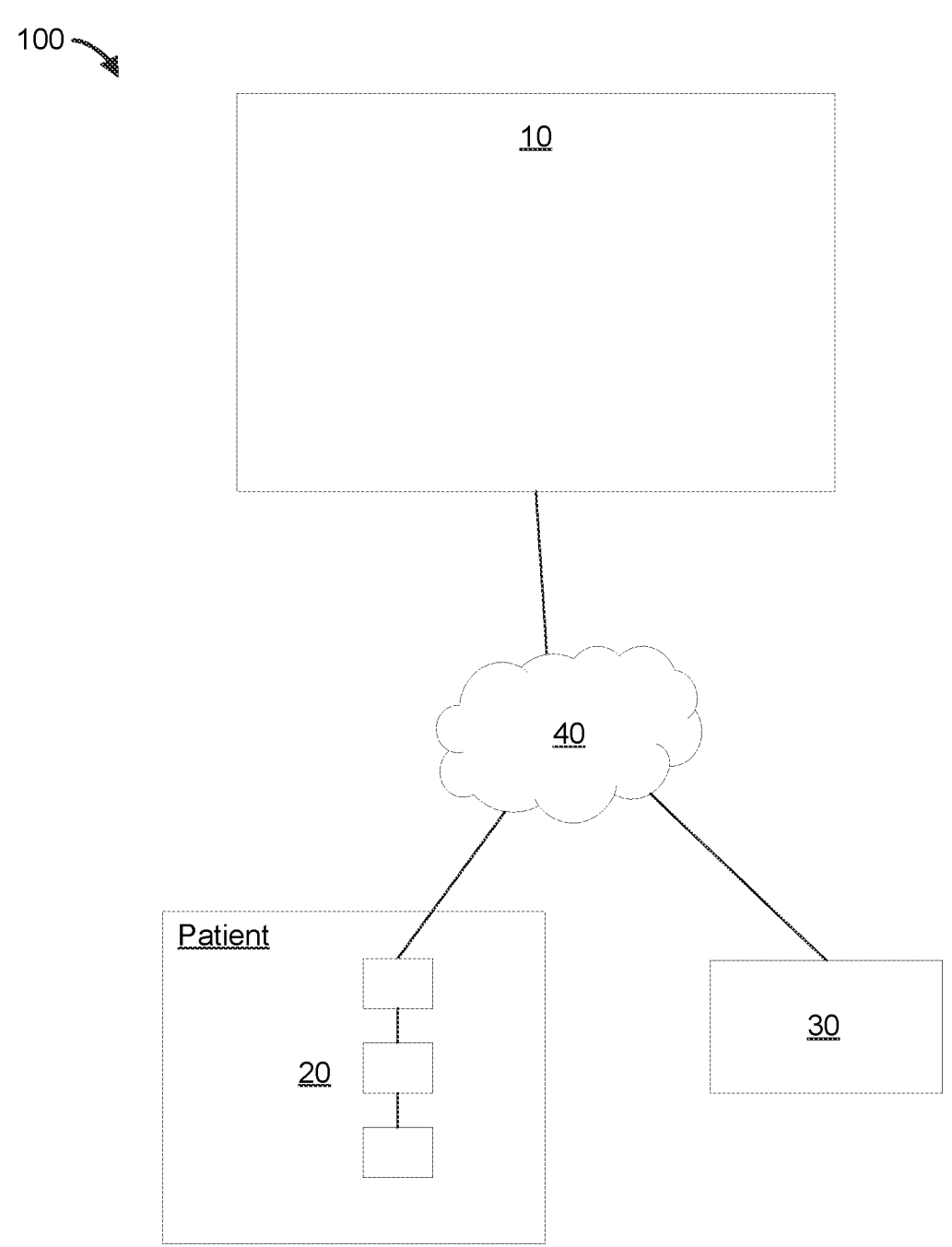
FIG. 1 is block diagram of an exemplary diagnostic system having a diagnostic tool and testing equipment, consistent with disclosed embodiments.

FIG. 1 is a block diagram of an exemplary diagnostic system 100. The diagnostic system 100 may include a diagnostic tool 10, a measurement tool 20, a data analysis tool 30, and a network 40. As described here, the diagnostic system 100 utilizes physics modeling of mechanical activity within a body of a patient. The diagnostic tool 10, measurement tool 20, and/or data analysis tool 30 may include computing devices configured to perform one or more steps of a process to provide a useful output for evaluating a patient based on measured and calculated data. The diagnostic tool 10 may be configured to receive measurement information from the measurement tool 20 and feedback information from the data analysis tool 30 and analyze the received information to produce a useful result helpful in evaluating the patient.

The measurement tool 20 may be a medical device configured to collect data from patient. For example, the measurement tool 20 may be an imaging device, such as an ultrasound imaging device. The measurement tool 20 may be configured to detect a patient response to an FMD process. The measurement tool 20, in some embodiments, may work in conjunction with the data analysis tool 30 to provide useful information to the diagnostic tool 10. For example, the measurement tool 20 may provide images or imaging data to the data analysis tool 30.

The data analysis tool 30 may analyze the images to determine values for one or more FMD variables. The FMD variables may be indicators of a patient's health, as described herein. The diagnostic tool 10 may receive the FMD variables and perform an analysis to provide useful information about the patient's heath. In some embodiments, the data analysis tool 30 may be integrated into the diagnostic tool 10.

The network 40 may be a communication device configured to connect the components of the diagnostic system 100, such as the diagnostic tool 10, the measurement tool 20, and/or the data analysis tool 30. The diagnostic tool 10, measurement tool 20, and data analysis tool 30 may each include a respective communications interface that are communicatively coupled to the network 40. In one or more cases, the communications interfaces may be configured to transmit and receive data to one or more other devices, such as, but not limited to, the diagnostic tool 10, measurement tool 20, and data analysis tool 30. The network 40 may be a wireless or wired communication device. In an exemplary embodiment, the network 40 is a wireless connection, such as one or more of WiFi, Bluetooth®, or the Internet. In other embodiments, the network 40 may include wired or integrated communication connections. The network 40 enables data communication between the components of the diagnostic system 100.

Figure 2:
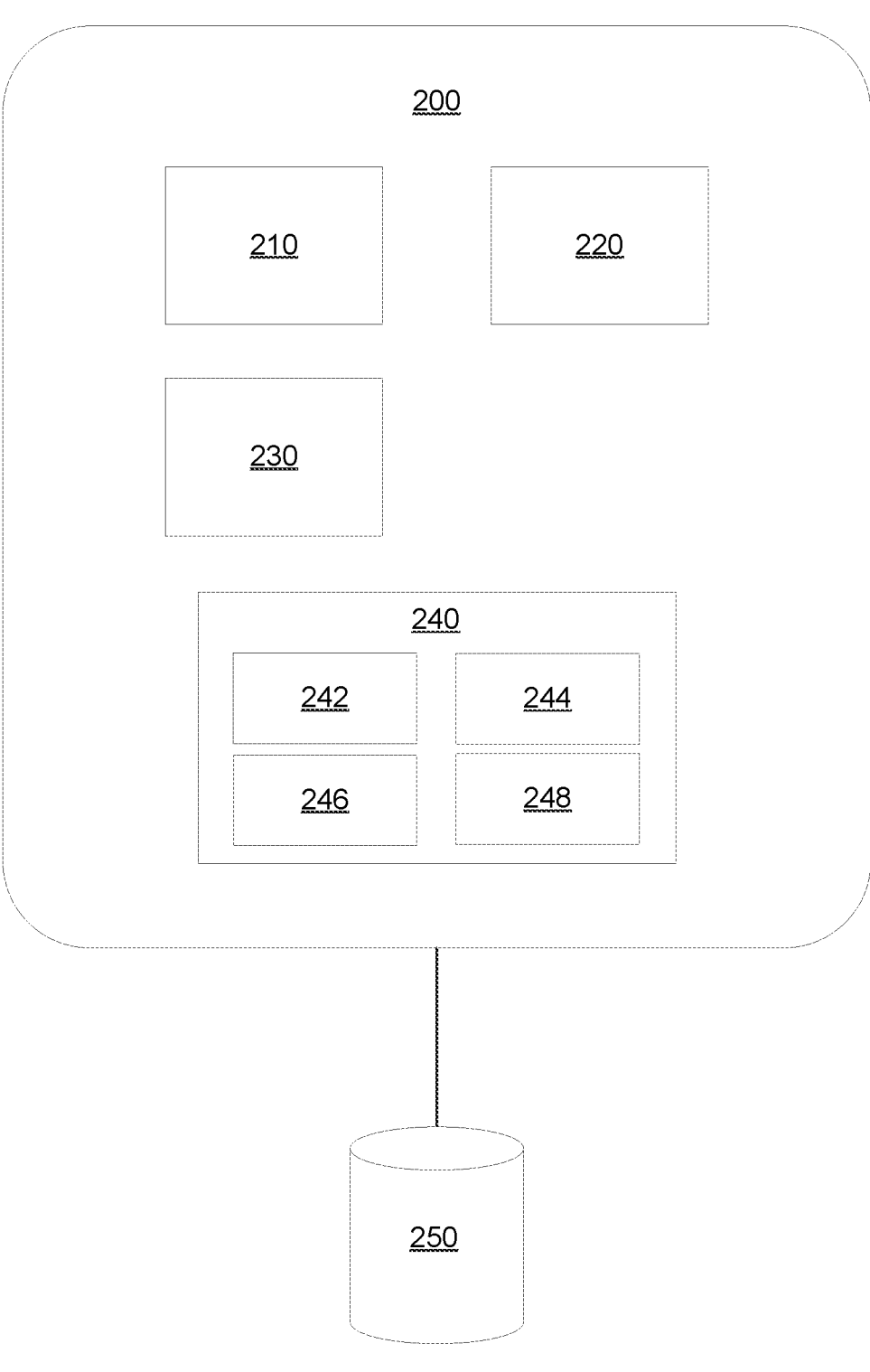
FIG. 2 is a block diagram of a computing device that may be used in conjunction with the diagnostic tool, consistent with disclosed embodiments.

FIG. 2 is a block diagram of an exemplary computing device 200. The computing device 200 may include at least a processing unit 210, a memory unit 220, and one or more input/output device 230. The computing device 200 may, in some embodiments, be connected to a database 250, such as a data repository. The computing device 200 may be representative of one or more of the diagnostic tool 10, the measurement tool 20, or the data analysis tool 30.

In an exemplary embodiment, the computing device 200 is an example of at least the diagnostic tool 10 and may include in whole or in part the measurement tool 20 and/or the data analysis tool 30. In some embodiments, the measurement tool 20 and/or the data analysis tool 30 are included via data connections at the input/output device(s) 230.

The computing device 200 may be a general or specialized computing system or component configured to receive information associated with an FMD process applied to a patient and provide output that is practically applicable to evaluating the health of the patient. In an exemplary embodiment, the computing device 200 includes a plurality of engines or modules 240 configured to perform processes for producing output based on measured input. The modules 240 may include, in an exemplary embodiment, a modeling module 242, an analysis module 244, an output module 246, and a learning module 248. The computing device 200 may include a digital user interface configured to display information, such as a diagnostic result of an FMD test, as described herein.

The modeling module 242 may be configured to use measurement data to model an effect of an FMD process applied to a patient. The modeling of the FMD process is further described herein. The modeling module 242 may be configured to use information from the data analysis tool 30 to determine one or more parameters related to the FMD process for a particular patient. The parameters may include (and are sometimes referred to herein as) FMD variables that are patient-specific measurements occurring as a result of the FMD process. In one example, the modeling module 242 may be configured to receive data from the data analysis tool 30 on the basis of images received by the measurement tool 20. The modeling module 242 may be configured to determine one or more parameters based on this data.

The analysis module 244 may be configured to receive the parameters determined by the modeling module 242 and identify an output to provide to a user of the diagnostic tool 10. For example, the analysis module 244 may be configured to compare the one or more parameters to one or more thresholds to determine a diagnostically-useful result of the FMD process. For instance, if a particular parameter is higher than a given threshold, the analysis module 244 may determine a particular risk factor associated therewith. The thresholds may be, for example, history, sex, etc. In some embodiments, the thresholds may be determined by the data analysis tool 30, such as based on patient-specific data input. For example, the data analysis tool 30 may retrieve a patient medical file and determine one or more thresholds to provide to the diagnostic tool 10. The various thresholds may be static or dynamic. For example, static thresholds may pertain to specific subgroups (e.g., categorized by age, ethnicity, gender, lifestyle, BMI, genetic predisposition, etc.) of healthy individuals. In some cases, the static thresholds may be determined based on controlled clinical studies, such that the modules provided herein, such as the analysis module 244, may evaluate the FMD parameters of healthy individuals in a given subgroup, and compare them to the parameter values corresponding to the patients belonging in the same subgroup, with various cardiovascular conditions and risk factors. In yet another example, as the modules allow for patient specific evaluations, a dynamic threshold may be determined based on moving averages of the parameter values obtained for a given individual over the course of several regular physical examinations that may include the BAFMD test. By determining the dynamic threshold based on moving averages, the modules may accommodate the given individual's normal aging process.

The output module 246 may be configured to provide the results produced by the analysis module 244 to a user. For example, the output module 246 may be configured to provide one or more data points determined based on threshold comparisons to a digital user interface viewable by the user. In one example, the output module 246 may be configured to output notifications associated with potential health risks determined based on the analysis module 244. In some embodiments, the output module 246 may be configured to provide a graphical representation of the measured parameters and/or the applied thresholds. For example, the output module 246 may provide a threshold range for a normal parameter and a marker denoting the measured parameter for the patient in relation to the threshold range.

The output module 246 provides a tangible medium for enabling the diagnostic tool 10 to practically apply the results of an FMD process to a diagnostic process. For example, the output module 246 provides a user with a quick and efficient result for diagnostic use based on an FMD process applied to a patient.

The learning module 248 is a feedback component configured to work in conjunction with other components of the diagnostic system 100 to improve the underlying processes. For example, the learning module 248 may be configured to provide data back to the data analysis tool 30, such as threshold comparison results or additional patient information input by the user. For example, a user may input actual health data for the patient that is indicative of patient health after the FMD process and analysis occurs. The learning module 248 may use the additional information to tune algorithms and processes for determining FMD variables and thresholds. In some embodiments, the learning module 248 may be configured to use machine learning and/or neural network processing to adjust the algorithms used to determine the FMD variables and/or thresholds for evaluating a patient's health.

The disclosed diagnostic system is related to the FMD process in which blood flow is cut off for a period of time in a patient's artery (e.g., brachial artery). The highly transient FMD process occurs at two main time scales, including that of a heartbeat (pulsation period) and that of the artery's dilation soon after the uncuffing process. Since arterial walls are not rigid, flow conditions will influence the artery's diameter change, which will in turn affect the flow conditions, making the problem fully coupled via a two-way fluid-structure interaction. The most challenging aspect of this system stems from the fact that, the arterial wall's mechanical properties are not constant throughout the FMD process, due to a physiological phenomenon known as the mechanotransduction. When the wall shear stress (WSS) changes, the endothelial cells (ECs) lining the arterial wall sense it, and through a complex network of biochemical signal pathways, instruct the artery's compliance to change accordingly. The microstructure through which ECs sense WSS, is the negatively charged Endothelial Glycocalyx Layer (EGL), a soft porous layer of proteoglycans and glycoproteins lining blood vessels' inner surface. In a set of in-vitro experiments, it has been shown that the EGL's structural configuration is indifferent to a disturbed flow lacking a forward component. Only when a forward shear stress was added during the FMD process, structural remodeling of the EGL could be observed. This preferential behavior towards forward (non-oscillatory) flows has also been observed when it comes to the ECs' shear-stress-induced release of the vasodilators responsible for increasing the compliance of arterial walls in response to an elevated WSS. A significant increase in vasodilation stimulation has been observed after a prolonged 24-hour exposure to a laminar flow. In another experimental study, it was shown that a steady laminar flow induced a nitric oxide (NO, a prominent vasodilator) synthesis that was dependent on the WSS magnitude (or step-change magnitude). On the other hand, upregulation of NO release failed when turbulent flow was introduced. On the flip side, reduced blood flow, as in congestive heart failure for example, flow mediated vasodilation is attenuated in-vivo. On the cellular level, mechanotransduction induced by WSS has been extensively studied via experimental investigations, analytical modeling, and numerical simulations. The EGL's physiological function as a mechanosensor and transducer has been well established. The transfer of fluid WSS at the EGL-fluid interface, through the matrix, to the form of solid stress in the endothelial cell's body has been described. Moreover, it has been shown that the EGL's presence is required for the ECs' responsiveness to WSS. Defective ECs have been shown to be unable to align themselves with a laminar flow even after a prolonged exposure. Atomic-scale molecular simulations have been used to discern the specific proteins acting as mechanosensors in the EGL. It was further established that the GPC1 core protein transmits the sensed shear stress to the EC's surface, resulting in NO production. Low shear stress has been shown to inhibit NO production, whereas high levels activate it. In the same study, when the aforementioned GPC1 core protein was removed, the effect that shear stress has on NO production was severely attenuated.

Figure 3:
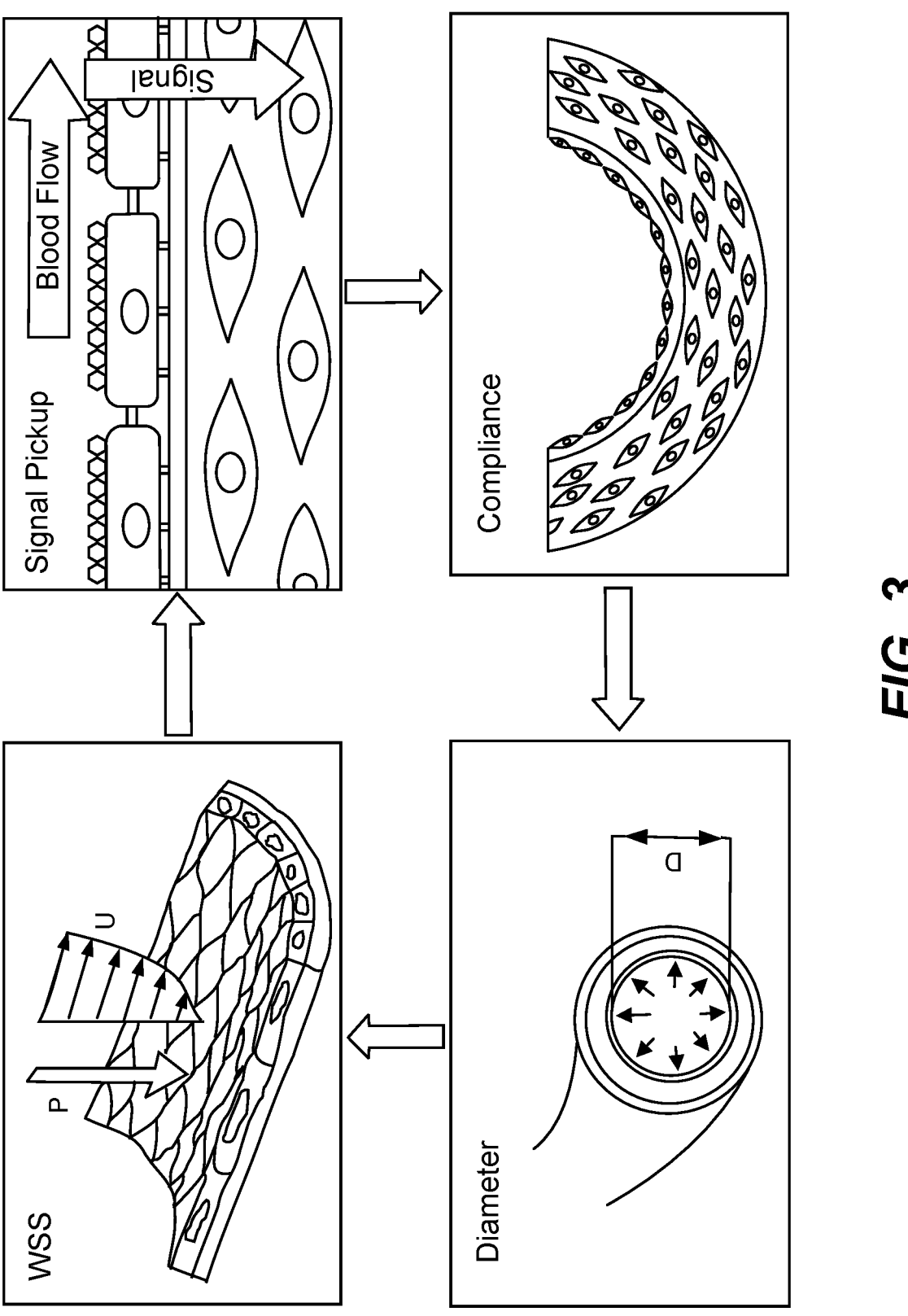
FIG. 3 is a hypothesized feedback loop describing the artery's response to changes in wall shear stress during the FMD process.
Figure 4A:
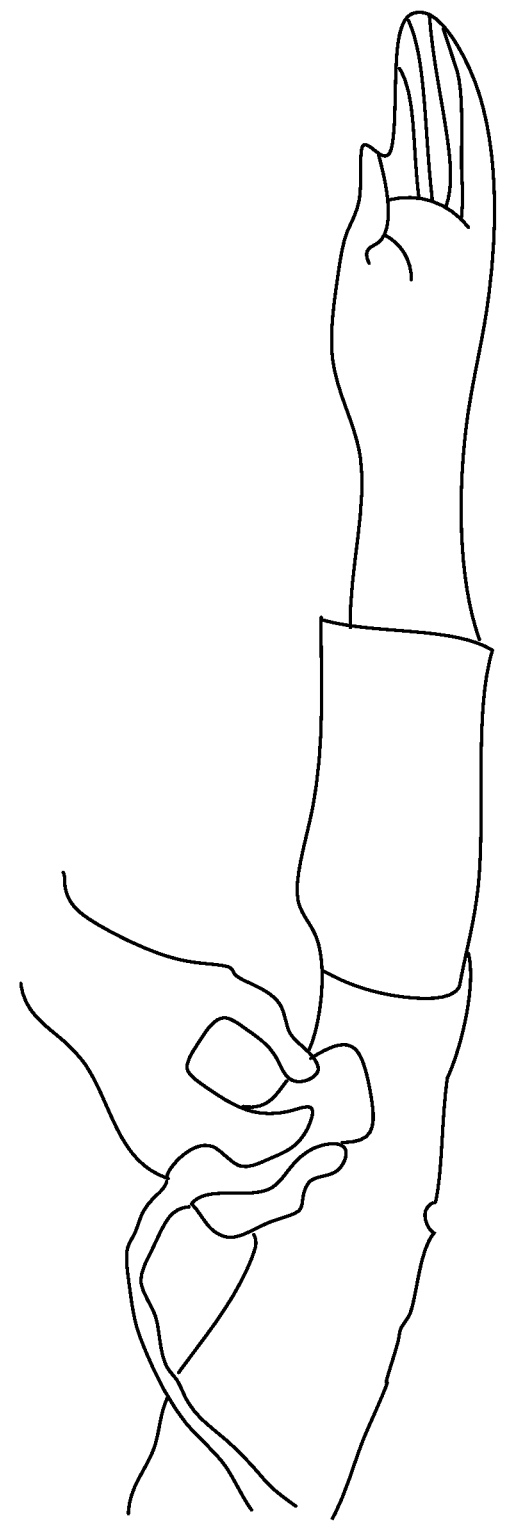
Figure 4A:
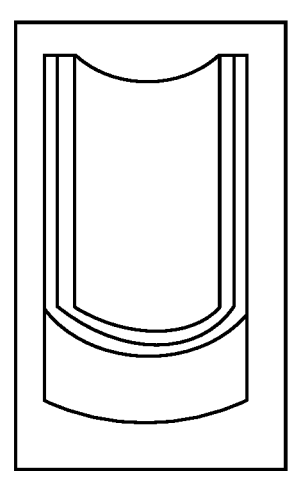
Figure 4A:
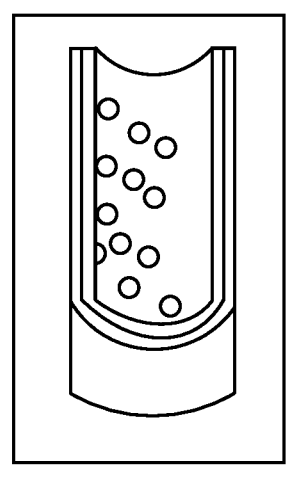
Figure 4A:
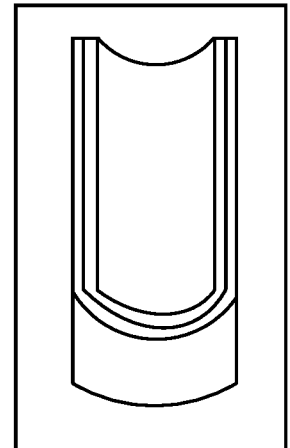
Figure 4B:
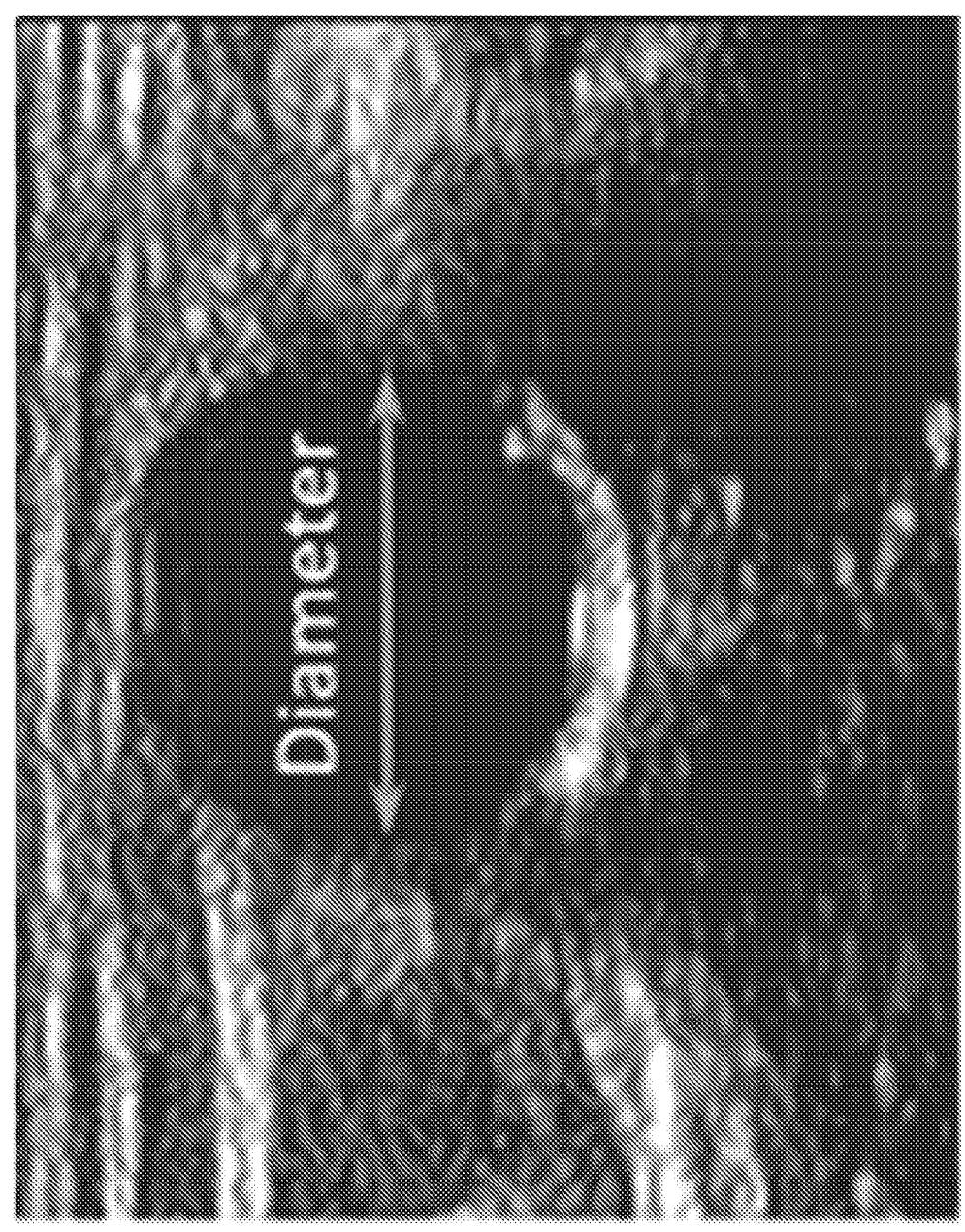
Figure 4C:
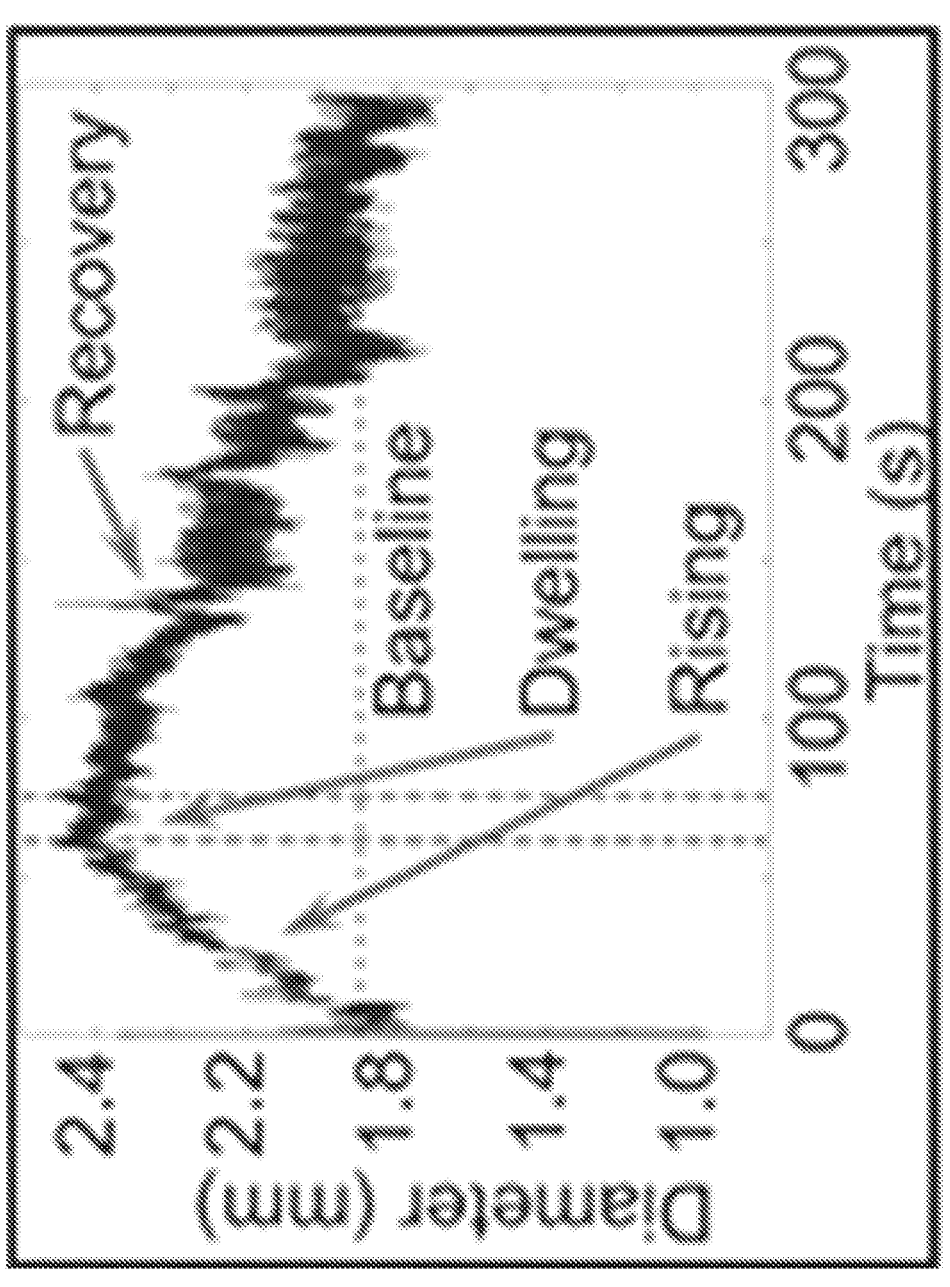

Collectively, the studies referenced above confirm the intimate dependence of the observed FMD response on the integrity of mechanotransduction taking place at the inner surface of the arterial wall, through sensing the highly transient changes in WSS levels after uncuffing. Guided by the knowledge acquired from all those studies probing mechanotransduction and vasodilator production on the microscopic level, the present disclosure relies at least in part on a feedback loop that macroscopically describes the mechanisms underlying the observed FMD response. FIG. 3 is a depiction of the feedback loop. When the blood flow is abruptly allowed back through the shrunken artery, the drastic WSS increase is picked up by the endothelial cells, initiating signal pathways that will stimulate the change of the mechanical properties (i.e. increasing compliance due to vasodilation stimulation) of the arterial wall. The artery's diameter would then respond by increasing under the fluid's pressure, and hence initiating dilation and decreasing the flow speed along with the WSS, which completes the feedback loop that makes FMD a self-modulating process.

Based on this, a physics-based model driven by the feedback loop depicted in FIG. 3 has been developed to describe the FMD response. This model was tested and observed in 5 healthy human subjects. The model correctly predicted a key feature in the beginning of the response that was experimentally observed across all subjects, and that conventional viscoelastic models fail to explain. Dimensionless parameters, each with a clear physical meaning, arose from the model. These dimensionless parameters can be used by the disclosed diagnostic system 100.

The evaluation of these parameters for each subject based on their FMD response, provided a quantitative description of the physical state of their artery. This evaluation links the microscopic underpinnings of endothelial mechanotransduction, to macroscopic observable, measurable, and physically meaningful quantities. While previous studies included some assumptions about arterial wall thickness, the present disclosure includes a diagnostic tool that utilizes a physics-based model describing the BAFMD response, in which the thickness of the arterial wall is not neglected. Mechanotransduction is accommodated by introducing a conceptual property, visualized to be radially diffusing throughout the arterial wall, thereby serving as the signal cueing compliance changes across the arterial wall's layers. In a study using this information, dimensionless parameters arising from the model, offering a quantitative assessment of the arterial wall's physical state, are evaluated for 12 healthy subjects, based on the 19 BAFMD responses that were obtained from them.

The present disclosure includes features derived in part from a patient study in which BAFMD processes were performed. The study was approved by the institutional review committee. BAFMD test was performed in the morning with all subjects fasting. The ultrasound scanner (ZONARE Medical Systems, Bernardo, CA, USA) was equipped with a broadband high resolution L14-5 MHz hockey stick transducer. Nineteen data sets were obtained from 12 healthy subjects aged 23-66. First, to make sure it was safe to perform the test, each subject, lying supine, had their blood pressure checked. While monitoring the brachial artery, an ischemic pressure cuff wrapped around their upper arm was inflated and maintained at 250 mmHg, as shown in FIG. 4(*a*). At the 5-minute mark, after the artery is completely shrunken, the cuff is suddenly deflated causing the blood flow to rush back into the artery. The recovery of the artery was monitored for about 2-5 minutes and recorded in video clips. FIG. 4(*b*) includes an image of the artery and FIG. 4(*c*) includes a graph of the recovery of the artery over time.

The video clips were processed for the Diameter vs. Time data in MATLAB. FIG. 4(*b*) illustrates how pixels inside the lumen stand out as darker than those corresponding to the surrounding tissue. This contrast in brightness was the main indicator used in the MATLAB codes that were written to extract the diameter at each frame. FIG. 4(*c*) shows a typical FMD response for 5 minutes after the cuff is deflated. The response features an initial, relatively sharp increase in the diameter, followed by a brief dwelling phase, and then a slow recovery to its baseline.

Figure 5:
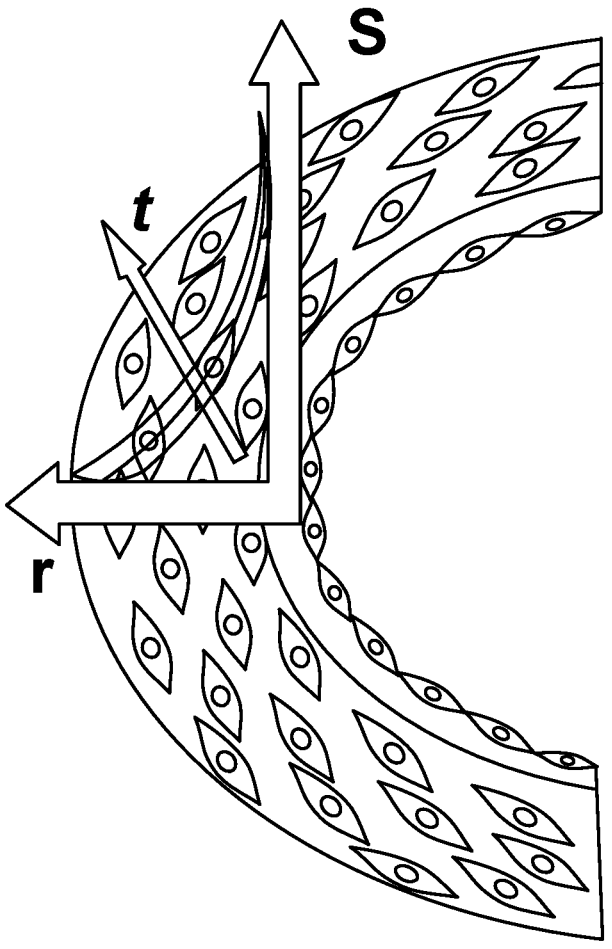
FIG. 5 is a visualization of the diffusion of the property s, along the radial direction r, as time t progresses, driven by the wall shear stress signal sensed at the wall's inner boundary.

As shown by the experimental studies cited above, sustained forward wall shear stress induces the release of vasodilators which in turn prompts the increase of the wall's compliance (the decrease of its stiffness). In the described study, considering mechanotransduction throughout the wall's thickness would require accounting for the time it takes the WSS signal picked up at the EGL to seep through the arterial wall. Since the biochemistry of vasodilators affecting smooth muscle cells is outside the scope of the proposed theory, a surrogate property, s (N/m$^2$), is visualized as diffusing radially throughout the wall's layers, delivering the "message" that these layers should soften (decrease their stiffness) accordingly. An illustration is shown in FIG. 5.

From its unit of stress, N/m$^2$, it can be seen that s is the equivalent shear stress that would be sensed by a certain location inside the wall if it were in contact with the blood flow, given that location's radial distance from the inner boundary. This is simply inspired from basic mass transfer principles based on which a diffusing substance's (in this case a vasodilator) concentration is attenuated as it diffuses away from the source. Since a higher value of WSS induces more vasodilator production, it can be seen why introducing this property as an alternate "messenger" is appropriate, and as will be evident shortly, theoretically convenient. A helpful analogy would be that the s surrogacy for the vasodilators' concentration, is like the temperature's surrogacy for the internal energy density. As the diffusion of s is intended to represent that of the vasodilators, the traditional first order diffusion law is assumed to govern it.

In cylindrical coordinates, s is then governed by Eq. 1:

$$\frac{\partial s}{\partial t} = \alpha_s \left( \frac{\partial^2 s}{\partial r^2} + \frac{1}{r} \frac{\partial s}{\partial r} \right) \tag{1}$$

where t(s) is time, r is the radial distance from the center, and $\alpha_s$(m$^2$/s) is the diffusivity.

Since s is equivalent to a sensed WSS at a distance as explained in the previous subsection, the same reasoning adopted in our precursor study, *Characterization of arterial flow mediated dilation via a physics-based model*, by Sidnawi, B., Chen, Z., Sehgal, C. & Wu, Q, *J. Mech. Behav. Biomed. Mater.* 107, 103756 (2020), the entirety of which is incorporated by reference herein, for the wall's lumped circumferential stiffness, will be applied here for the modulus of elasticity $E(N/m^2)$. The value of the local modulus of the wall, $E_s(s)$, that would be reached if exposure to s is sustained (denoted by the s subscript in $E_s$) for a long period of time, is assumed to take an exponential decreasing function from a maximum value $E_0$ for s=0, to a minimum asymptotic value, $E_\infty$, as s→∞. This depicts the softening effect that WSS (driving the diffusion of s) has on the arterial wall. Eq. 2 below governs $E_s$.

$$E_s(s) = (E_0 - E_\infty)e^{-\beta s} + E_\infty \tag{2}$$

Figure 6:
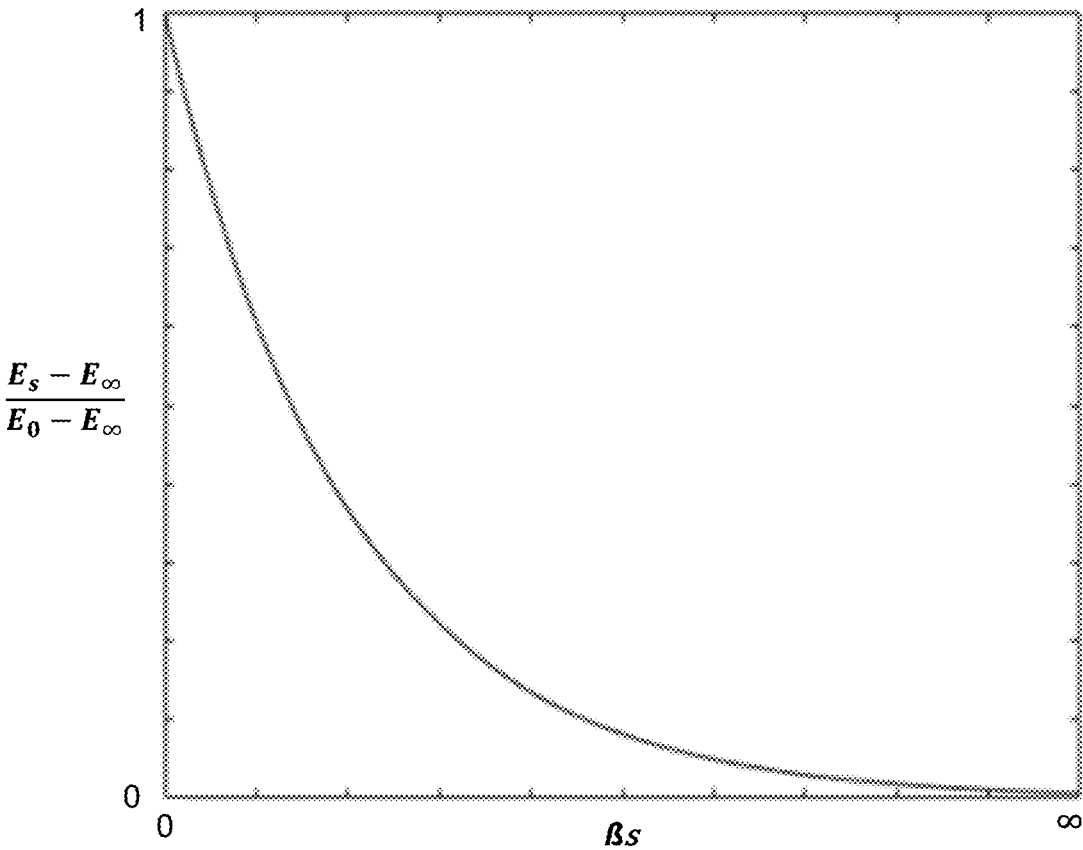
FIG. 6 is a graphical representation of the assumed behavior of $E_s$ in response to s.

$\beta(m^2/N)$ is a characteristic property that indicates the wall's resistance to a changing value of s. a higher value means a lower resistance. This behavior is illustrated in the graph of FIG. 6.

Figure 7:
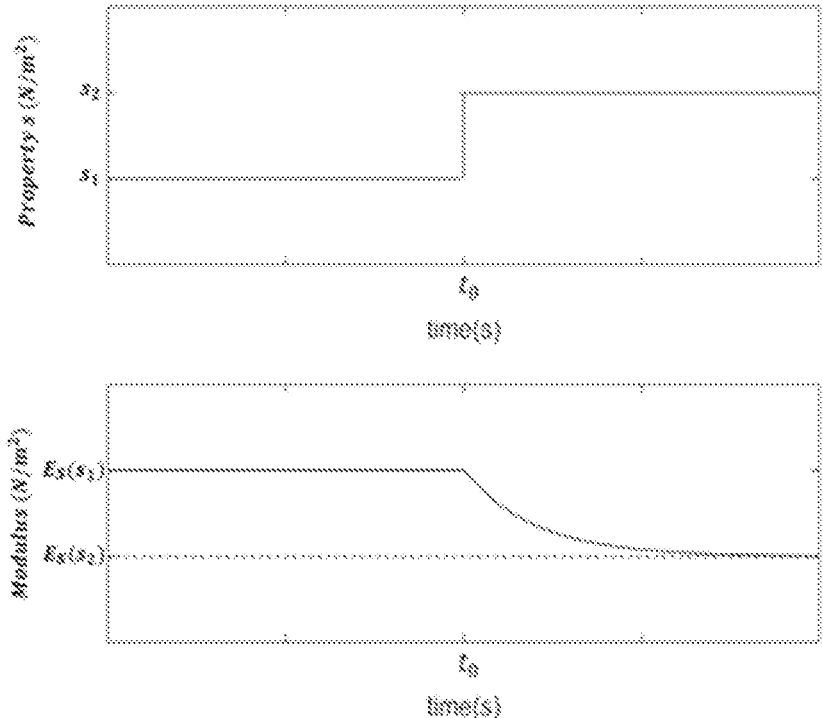
FIG. 7 is a graphical representation of the time response E(t) to a step-change in the value of s.

The instantaneous value of the modulus, $E(t)$, like many physiological processes, is expected to be transient. This means that after a sustained exposure to a value $s_1$ of s, entailing a modulus value of $E_s(s_1)$ (Eq. 2), if at $t=t_0$, s suddenly shifts to a new value $s_2$, the modulus would take some time to reach $E_s(s_2)$ as illustrated in FIG. 7.

For $t \geq t_0$, the shape of this response is also assumed to be exponential as follows:

$$E(t) - E_s(s_2) = (E_s(s_1) - E_s(s_2))e^{-\xi(t-t_0)} \tag{3}$$

$\xi(s^{-1})$ is a property of the artery that quantifies its responsiveness to a changing WSS. A greater value of $\xi$ indicates a more responsive artery. In a similar procedure to that followed in the *Characterization of arterial flow mediated dilation via a physics-based model* study, by thinking of a s(t) time signal as a series of infinitesimal steps, the equation governing $E(t)$ in response to any function s(t) can be derived from Eqs. 1 and 2. According to Eq. 1, at any instant during a transient response $E(t)$ the following holds: $E_\infty < E(t) < E_0$. Therefore, for any value that $E(t)$ takes, there exists a value of s, ŝ such that:

$$E(t) = E_s(\hat{s}) \tag{4}$$

the incremental change in E is: $dE = E(t+dt) - E(t)$, which from Eq. 3 becomes:

$$dE = E(t+dt) - E_s(\hat{s}) \tag{5}$$

Applying Eq. 3 to the difference in Eq. 5, one obtains $$E(t+dt) - E_s(\hat{s}) = (E_s(\tau) - E_s(\hat{s}))(1 - e^{-\xi dt}) \tag{6}$$

Hence, substituting Eq. 4 into Eq. 6, $$dE = (E_s(s) - E(t))(1 - e^{-\xi dt}) \tag{7}$$

Expanding $e^{-\xi dt}$ into a Maclaurin series and only retaining the first order term as dt→0, $$dE = (E_s(s) - E(t))\xi dt \tag{8}$$

or, $$\frac{dE}{dt} + \xi E = \xi E_s(s(t)) \tag{9}$$

The rising-and-dwelling part of the observed FMD response for all cases is a slow process. This behavior makes it reasonable to assume that the expanding arterial wall is in a quasi-static equilibrium between the internal pressure pushing it outwards, and the opposing elastic forces resisting the deformation. When the blood flow $q(m^3/s)$ is allowed back in, the WSS will be at its highest level. As the resulting diffusion of s takes place, the arterial layers will gradually soften, and the artery will therefore expand to maintain the balance between its wall's internal elastic forces and the blood pressure, decreasing the WSS in the process.

Since a purely oscillatory WSS, devoid of a forward component, has been shown to be incapable of stimulating vasodilation, only the steady components of the WSS and local pressure signals will be considered in this study. Also, with the subject lying in a restful state, and the artery being back open, allowing blood flow to the lower arm branch of the body to be reestablished, the steady component of the pressure signal at the examined location of the brachial artery will be assumed to be constant. This is because the steady component of the pressure drop from the heart's left ventricle over the fixed distance to the examined location of the brachial artery near the elbow can be reasonably assumed constant with the steady component of the blood flow rate, q, reestablished to that branch of the body.

The problem is setup as an initially undeformed cylindrical shell with an inner radius, $r_{in}(m)$, and outer radius, $r_{out}(m)$. A sketch is shown in the FIG. 8.

At t=0, an internal pressure $p(N/m^2)$ with a flow rate q are imposed. As the expansion is quasi-static, the steady component of the wall shear stress, $\tau_w(N/m^2)$, would correspond to the parabolic velocity profile in a Poiseuille flow:

$$\tau_w(t) = \frac{4\mu q}{\pi R(t)^3} \tag{10}$$

where $\mu(kg/m\cdot s)$ is the blood's dynamic viscosity, and R(t) is the inner deformed radius. $\tau_w(t)$ is in fact $s(r_{in},t)$. If $u(r,t)$ denotes the radial displacement, and $u_0(t)$ denotes the displacement of the inner boundary, then $R(t) = r_{in} + u_0(t)$ and Eq. 10 may be rewritten as:

$$s(r_{in}, t) = s_0 \left( \frac{r_{in}}{r_{in} + u_0(t)} \right)^3 \tag{11}$$

where $$s_0 = \frac{4\mu q}{\pi r_{in}^3}.$$

The system of equilibrium equations governing the wall's expansion is:

$$\frac{\partial \sigma_{rr}}{\partial r} + \frac{1}{r}\frac{\partial \sigma_{r\theta}}{\partial \theta} + \frac{1}{r}(\sigma_{rr} - \sigma_{\theta\theta}) = 0 \tag{12a}$$

$$\frac{1}{r}\frac{\partial \sigma_{\theta\theta}}{\partial \theta} + \frac{\partial \sigma_{r\theta}}{\partial \theta} + \frac{2}{r}\sigma_{r\theta} = 0 \tag{12b}$$

Figure 8:
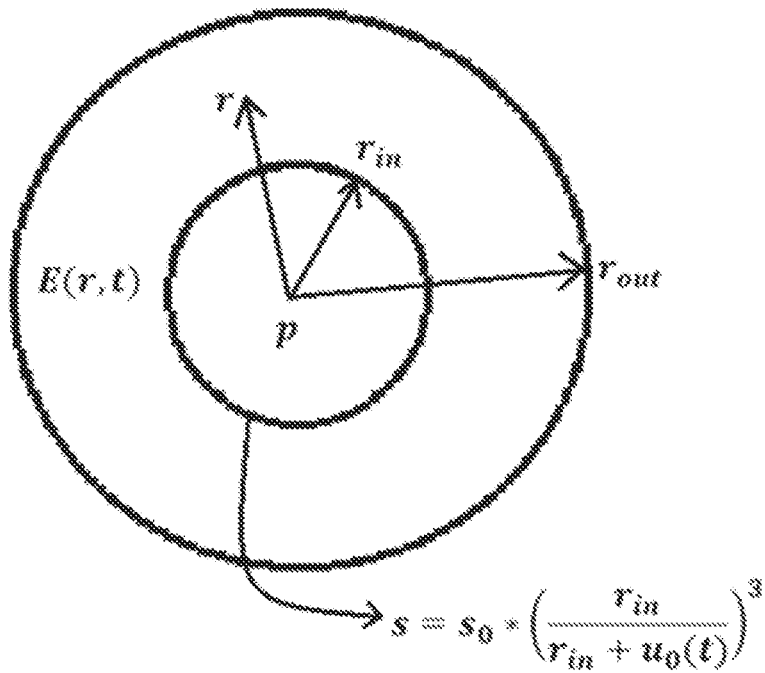
FIG. 8 is a sketch of an arterial wall being modeled for mechanical effects of FMD.

11 where $\sigma$ is the stress tensor, and $\theta$ is the orthoradial coordinate. The wall's constitutive equations are those given by the standard elasticity theory:

$$\begin{bmatrix} \sigma_{rr} \\ \sigma_{\theta\theta} \\ \sigma_{r\theta} \end{bmatrix} = \begin{bmatrix} \dfrac{E}{1-v^2} & \dfrac{Ev}{1-v^2} & 0 \\ \dfrac{Ev}{1-v^2} & \dfrac{E}{1-v^2} & 0 \\ 0 & 0 & \dfrac{E}{v+1} \end{bmatrix} \begin{bmatrix} \varepsilon_{rr} \\ \varepsilon_{\theta\theta} \\ \varepsilon_{r\theta} \end{bmatrix} \qquad (13)$$

where E is the elasticity modulus, treated as a variable quantity as illustrated in FIG. 8, $v$ is Poisson's ratio, assumed to take on the typical value of about 0.3 in this study, and $\varepsilon$ is the strain tensor. As the problem is axisymmetric, dependence on $\theta$ vanishes $$\left(\frac{\partial}{\partial\theta} = 0\right).$$

Also, the shear stress, $\sigma_{r\theta}$ would have to assume the same value in both clockwise and counterclockwise directions, since axisymmetry renders both directions equivalent. This can only be possible if $\sigma_{r\theta}=0$. Recognizing that $$\varepsilon_{rr} = \frac{\partial u}{\partial r}, \text{ and } \varepsilon_{\theta\theta} = \frac{u}{r},$$

then substituting Eq. 13 in Eq. 12a, the wall's equilibrium equation becomes:

$$\frac{\partial^2 u}{\partial r^2} + \left(\frac{1}{E}\frac{\partial E}{\partial r} + \frac{1}{r}\right)\frac{\partial u}{\partial r} + \left(\frac{v}{Er}\frac{\partial E}{\partial r} - \frac{1}{r^2}\right)u = 0 \qquad (14)$$

Substituting Eq. 10 in Eq. 2, the equation governing E(r, t) is obtained as:

$$\frac{\partial E}{\partial t} + \xi E = \xi\left[(E_0 - E_\infty)e^{-\beta s} - E_\infty\right] \qquad (15)$$

the following dimensionless variables are introduced:

$$r^* = \frac{r}{r_{in}}, t^* = \frac{\xi t}{2\ln(10)}, u^* = \frac{u}{r_{in}}, E^* = \frac{E}{E_0}, s^* = \frac{s}{s_0} \qquad (16)$$

where $r^*$ is the dimensionless radial position, $t^*$ is the dimensionless time, $u^*$ is the dimensionless radial displacement, $E^*$ is the dimensionless radial modulus, and $s^*$ is the dimensionless surrogate property.

Note that the time scale, $$T = \frac{2\ln(10)}{\xi},$$

is the solution to $e^{-\xi T}=\phi$ where $\phi$ is chosen to be $\phi=0.01$. There is nothing further to be read into this is choice. It is arbitrary. Substituting Eq. 16 into Eqs. 1, 14, and 15, the system of equations governing the FMD process is obtained:

12

$$\frac{\partial^2 u^*}{\partial r^{*2}} + \left(\frac{1}{E^*}\frac{\partial E^*}{\partial r^*} + \frac{1}{r^*}\right)\frac{\partial u^*}{\partial r^*} + \left(\frac{v}{E^* r^*}\frac{\partial E^*}{\partial r^*} - \frac{1}{r^{*2}}\right)u^* = 0 \qquad (17a)$$

$$\frac{\partial E^*}{\partial t^*} + 2\ln(10)E^* = 2\ln(10)\left[(1 - E^*_{min})e^{-Bs^*} + E^*_{min}\right] \qquad (17b)$$

$$\frac{\partial s^*}{\partial t^*} = 2\ln(10)\gamma\left(\frac{\partial^2 s^*}{\partial r^{*2}} + \frac{1}{r}\frac{\partial s^*}{\partial r^*}\right) \qquad (17c)$$

The arising dimensionless parameters are:

$$E^*_{min} = \frac{E_\infty}{E_0}, B = \beta s_0, \gamma = \frac{\alpha_s}{r^2_{in}\xi}, a = \frac{r_{out}}{r_{in}}, p^* = \frac{p}{E_0} \qquad (18)$$

From its expression, $$E^*_{min}$$

indicates how sensitive the arterial wall is to WSS. The closer $$E^*_{min}$$

is to its maximum value of 1, the more indifferent the wall is to the sensed WSS. Since B, the parameter that indicates the artery's resistance to a changing WSS, is directly related to $\beta$, a higher value would indicate a wall that is less resistant to softening by an increasing WSS. $\gamma$ is the parameter that quantifies the integrity of mechano-transduction. A higher value of $\gamma$ indicates a faster diffusion of the property s, thus pointing to a more active mechanotransducion.

At the inner boundary, s is determined from Eq. 11, and at the outer boundary, s cannot diffuse any further and therefore, $$\frac{\partial s}{\partial r}(r_{out}, t) = 0.$$

In dimensionless form, the boundary conditions for s* are:

$$s^*(1, t) = \left(\frac{1}{1 + u^*_0(t^*)}\right)^3 \qquad (19a)$$

$$\frac{\partial s^*}{\partial r^*}(a, t) = 0 \qquad (19b)$$

The normal radial stress at the inner boundary is determined from the inside pressure p as $\sigma_{rr}(r_{in},t)=-p$. The outer boundary is load free and therefore $\sigma_{rr}(r_{out},t)=0$. Using Eqs. 13 and 18, the dimensionless form of the boundary conditions for u* are:

$$\left(\frac{\partial u^*}{\partial r^*} + v\frac{u^*}{r^*}\right)\bigg|_{r^*=1} = \frac{(v^2 - 1)p^*}{E^*(1, t)} \qquad (20a)$$

$$\left(\frac{\partial u^*}{\partial r^*} + v\frac{u^*}{r^*}\right)\bigg|_{r^*=a} = 0 \qquad (20b)$$

At t=0, no diffusion of s has occurred yet which means s(r,0)=0, and therefore no softening has taken place meaning E(r,0)=$E_0$. The dimensionless form of the initial conditions for E and s are then obtained as:

$$E^*(r^*,0)=1 \tag{21a}$$

$$s^*(r^*,0)=0 \tag{21b}$$

However, at t=0, the inside pressure p will cause an initial deformation while the entire vessel wall is still at a uniform modulus, $E_0$, which means $$\frac{\partial E}{\partial r}(r, 0) = 0.$$

This makes the initial form of Eq. 17a an ordinary equidimensional differential equation whose solution in dimensionless form yields the initial condition for u*:

$$u^*(r^*, 0) = \frac{p^*}{a^2 - 1}\left[(1 - v)r^* + (1 + v)\frac{a^2}{r}*\right] \tag{22}$$

The system of equations in Eq. 17 will be solved subject to the boundary conditions given by Eqs. 19 and 20, and the initial conditions given by Eqs. 21 and 22. Finite difference is used for the numerical solution of Eq. 17. The arterial wall is discretized along the radial direction, with a grid size $\delta r^*$ separating two consecutive nodes. Time is discretized into instants separated by a timestep $\delta t^*$. The discrete counterparts of all space derivatives in Eq. 17 are based on a truncation error of $0(\delta r^{*3})$. At every timestep Eq. 17a is discretized into a linear system of equations to obtain the displacement u* at each node. Eqs. 17b and 17c are then solved to obtain E* and s*, respectively, at each node by the next timestep, and so the solution proceeds for the remainder of the chosen duration. However, the choices of the grid size, $\delta r^*$, and the timestep, $\delta t^*$, are not decoupled. To guarantee the stability of the diffusion equation's solution (Eq. 17c), the upper bound, $$\delta t^*_{max},$$

of the timestep, for a given grid size, $\delta r^*$, is imposed as:

$$\delta t^*_{max}, = \frac{1}{4\gamma\ln(10)\left(\frac{1}{\delta r^{*2}} - \frac{1}{2\delta r^*(1 + \delta r^*)}\right)} \tag{23}$$

Figure 9:
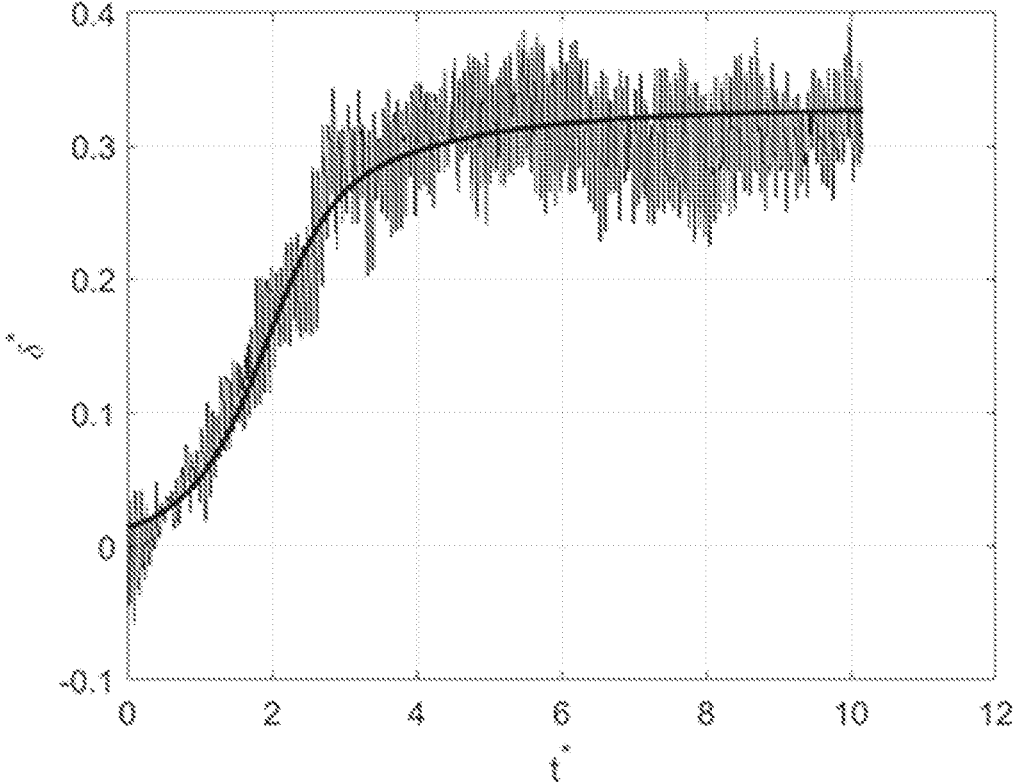
FIG. 9 is a graph of a representative result of fitting the theoretical response to its observed counterpart.

For the rising-and-dwelling part of each of the experimental FMD responses, d(t), obtained in this study, the parameters in Eq. 18, were optimized to the values that resulted (through solving Eq. 17) in the closest theoretical response, $u^*(0,t^*)=\delta^*(t)$, to its observed counterpart. FIG. 9 shows a representative result for one of the subjects after fitting a theoretical response to the one observed experimentally. The thick solid curve is the theoretical response.

As evident from FIG. 9, the curvature shift in the beginning of the response, a distinctive manifestation of mechanotransduction, is independently predicted by the proposed model. Since it takes time for the WSS signal to reach into the wall and initiate the required softening of the tissue, the artery's expansion starts at a slow rate before picking up speed. This behavior was observed in all 19 cases considered for this study. The remaining 18 fitting results are shown in FIGS. 18a-18r, in which the labeling convention for the subjects who had repeat tests is: Subject Number—Test Number (e.g., FIGS. 18b and 18c are graphed results for Subject 3 who underwent two tests, Test 1 and Test 2). In addition to the correctly predicted curvature shift, serving as one piece of experimental evidence in favor of the proposed model, α, the artery's outer-to-inner diameter (unstretched) ratio was also predicted within a reasonable margin. For each of the 19 cases, the obtained ultrasound clip of the arterial response was rewound back to a stage within the slow part of the response before the curvature shift. This is the closest one could get to an in-vivo non-invasive measurement of α, for an unloaded arterial wall. The comparison results of predicted vs. measured values of α are shown in the FIG. 10.

Figure 10:
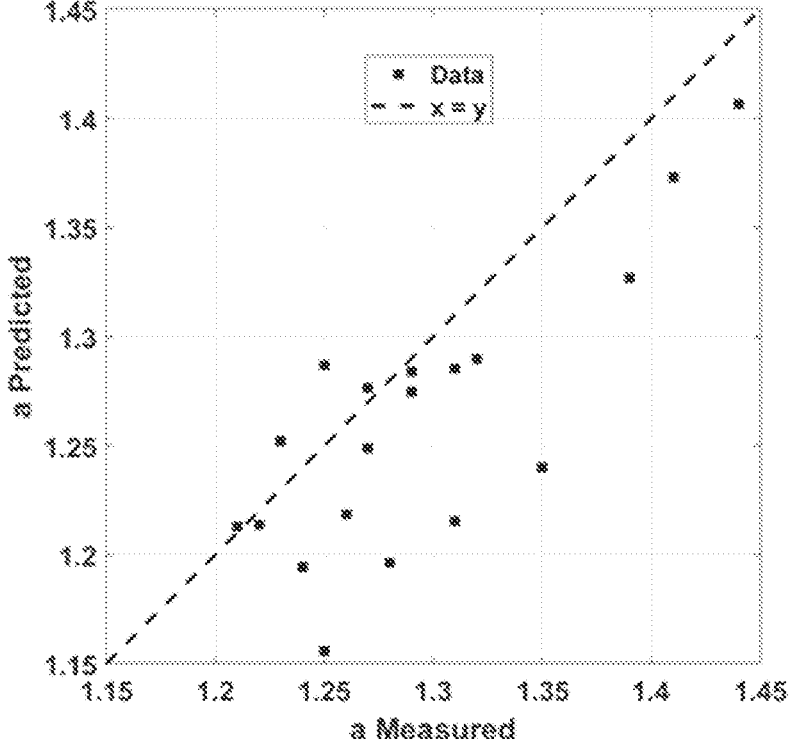
FIG. 10 is a graph of predicted v. measured values of the arterial outer-to-inner diameter ratio, $\alpha$.

Although a scatter in the data shown in FIG. 10 is noticeable, a majority of the data points follow the first bisector's trend (y=x). Since 12 subjects were recruited for this study, some of the 19 collected responses were repeat tests. The results for the predicted value of α for each of the subjects are shown in FIG. 11.

Figure 11:
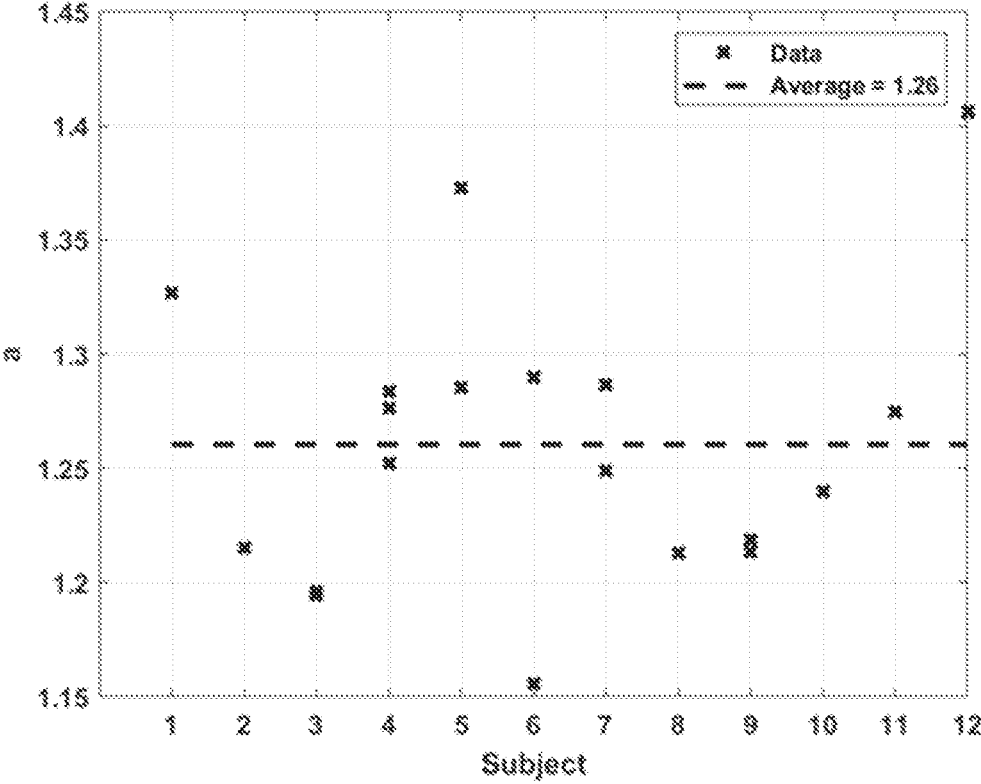
FIG. 11 is a graph of predicted arterial outer-to-inner diameter ratio, $\alpha$ for all subjects.

As shown in FIG. 11 the average predicted value of α is about 1.26. Subjects, 3-7, and 9 had repeat tests, all of which show good repeatability except for subjects 5 and 6. However, for subject 6, one of the tests had a measured value of 1.25 vs. a predicted value of 1.16, while the second test had a measured value of 1.32 vs. a predicted value of 1.28. Subject 5 on the other hand, had a measured value of 1.41 vs. 1.37 predicted for one test, while the other test showed a measured value of 1.31 vs. 1.29 for the predicted value. This is a reminder of the trivial fact that the repeatability of the prediction results is tied to that of the experimental measurements. A quite plausible reason for the occasional variability in the measurements of α is that the arterial wall is not a straight prismatic cylindrical shell of identical dimensions at every location along its axis. Therefore, in addition to the artefacts in the ultrasound images, that could slightly throw off the measurements, it is also not a certainty that the transducer was placed at the exact same spot on the subject's arm during both tests.

Figure 12:
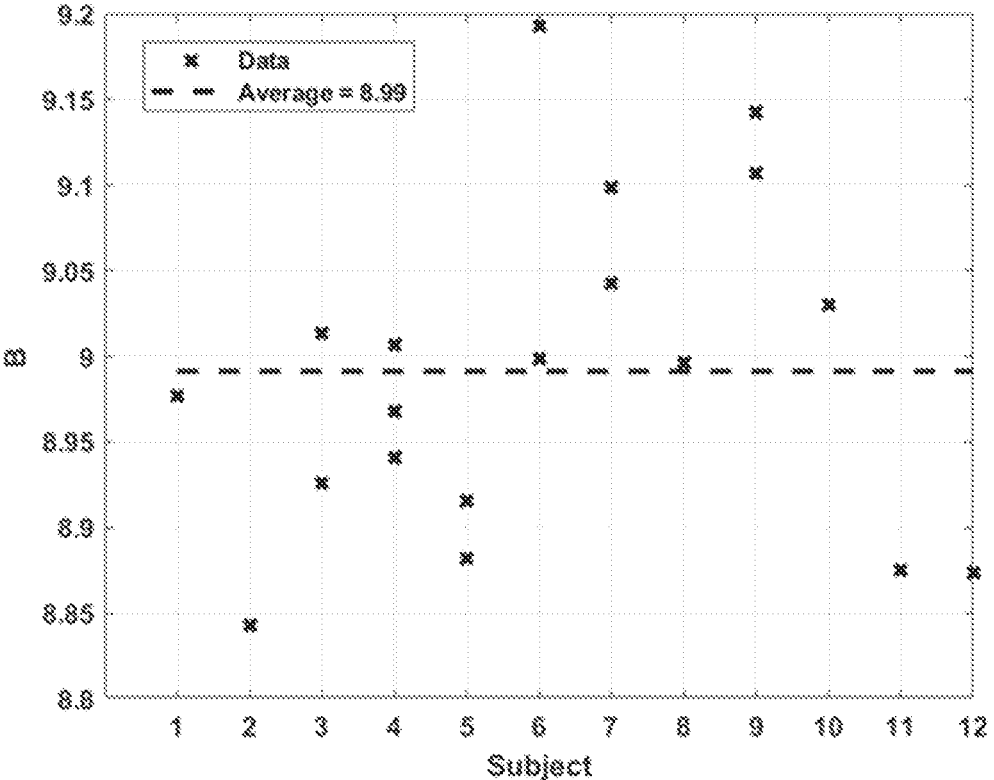
FIG. 12 is a graph of predicted value of B for all subjects.

The results for B, the parameter that indicates the artery's resistance to a changing WSS, with a lower value pointing to higher resistance since it is directly related to β (Eqs. 2 and 18), are shown in FIG. 12 for all subjects.

The average value predicted for B is 8.99, ranging from about 8.85 to 9.2. Given the tight range for B, good repeatability for the same subject and across different subjects is observed.

$$E^*_{min} = E_\infty/E_0$$

Figure 13:
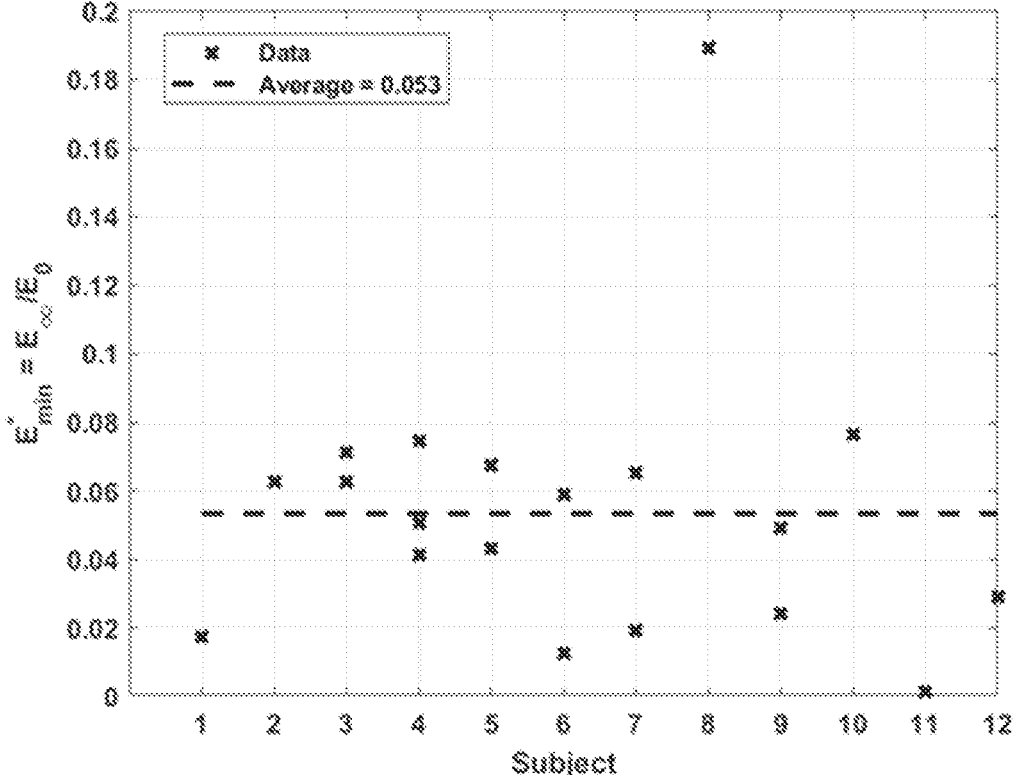
FIG. 13 is a graph of predicted value of $$E^*_{min}$$

(Eq. 18), is the parameter that indicates the sensitivity of the arterial tissue to WSS, in which a higher value points to an arterial wall that is more indifferent to an increasing shear stress. The values extracted for this parameter are shown in FIG. 13.

An average value of $E^*_{min}$ in predicted for all subjects is about 0.053, with data points reasonably tight around the average line. It is not immediately clear why the value corresponding to subject 8 is so far off. The most plausible reason though could be one of the uncertainties mentioned earlier about the noisy ultrasound images.

15

The results for $$\gamma = a_s/r_{in}^2 \xi$$

(Eq. 18), the parameter quantifying the integrity of mechanotransduction, are shown in FIG. 14. A higher γ value points to an arterial wall that is more permeable to the WSS signal instructing the tissue to soften up.

γ had an average predicted value of about 0.0017. Roughly all the predicted values for this parameter lie within the same order of $10^{-3}$. Like in the case of the ratio α, repeatability for subjects 5 and 6 stands out as quite different from the other subjects. However, there seems to be a sensible connection between the 2 parameters. For both subjects, the higher value of γ, corresponds to the test where a greater value of α was measured. A possible explanation for this behavior could be that in the same artery, when the wall at given cross-section is thicker than another, γ increases accordingly to make up for the greater distance the signal s needs to travel; thereby keeping the artery's response along its axis as homogenous as possible. Interestingly, the γ values pertaining to all the other subjects who had repeat tests, consistently exhibited the same behavior.

The present disclosure includes the *Characterization of arterial flow mediated dilation via a physics-based model* study for determining exemplary parameters (FMD variables) that provide information about a patient in response to an FMD process. The following description includes a parametric study that further analyzes the applied model and results. In addition to the response $\delta^*(t^*)=u^*(0,t^*)$, all the figures in this section show the profiles of s* and E* at the last time step of the simulation. FIG. 15 includes the effects of a changing value for B.

Since B is directly related to β (Eq. 18), a higher value means a lower arterial resistance to a changing WSS. Therefore, as evident from the E*(r*) profile, the artery gets softest for the highest value of B, and consequently the artery undergoes the highest deformation ($\delta^*(t^*)$). Also, notice how for all values of B, the artery is softest (E*(r*)) towards the inner radial locations where s* is highest (strongest vasodilation stimulation). The slight effect that B has on s* is due to the changing deformation at r*=1, affecting the WSS (Eq. 11).

FIG. 16 includes the effects of a changing value for $$E_{min}^*.$$

As mentioned earlier, $$E_{min}^*$$

quantifies the sensitivity of the arterial wall to a changing WSS. At its maximum value of 1, where $E_\infty=E_0$, the arterial compliance is completely indifferent to WSS. This is manifested by E*(r*) holding a flat profile leading to a corresponding flat unchanging deformation ($\delta^*(t^*)$). The lower the value of $$E_{min}^*$$

16 gets, the softer the arterial wall eventually becomes (E*(r*)), allowing for further deformation ($\delta^*(t^*)$). As in the case of B, changing $$E_{min}^*$$

has little effect on the diffusion of s*.

FIG. 17 includes the effects of a changing value for γ. γ is the parameter characterizing mechanotransduction. Since it is directly related to the diffusion coefficient, $\alpha_s$, of the property s, a higher value indicates a faster diffusion and therefore a more robust mechanotransduction. Note how at the highest value of γ, the s*(r*) profile gets closest to becoming uniform, prompting the profile E*(r*) to follow suit, and consequently leading to the highest deformation ($\delta^*(t^*)$).

In the embodiments described herein, a model describing mechanotransduction in a thick arterial wall during flow mediated dilation is proposed. Each of the parameters that arise from the proposed model has a specific physical meaning that pertains to an aspect of the arterial wall's physical state. Particularly, a parameter directly quantifying the integrity of mechanotransduction emerged from the model. 19 arterial responses were collected from 12 healthy subjects who underwent the BAFMD test. Using an optimization algorithm, the parameter values corresponding to each of the experimentally observed responses were found. The resulting theoretical responses show that the model independently predicts a distinctive feature of mechanotransduction, that was observed across all the considered cases.

The embodiments include an example method for determining a plurality of parameters that can be used to describe the physical status of a patient, and, in particular, their health status, based on the physical reaction of their artery to FMD. For example, the embodiments produce, among other parameters, $$E_{min}^*,$$

B, and γ. From its expression, $$E_{min}^*$$

indicates how sensitive to WSS the arterial wall is. The closer $$E_{min}^*$$

is to its maximum value of 1, the more indifferent the wall is to the sensed WSS. Since B is directly related to β, a higher value would indicate a wall that is less resistant to softening by an increasing WSS. γ is the parameter that quantifies the integrity of mechanotransduction. A higher value of γ indicates a faster diffusion of the property s, thus pointing to a more active mechanotransduction.

These parameters are thus examples of quantified measures of a patient's health based on BAFMD. As described above, these parameters can be described as a sensitivity, resistance, and integrity. Disclosed embodiments may include additional processes to populate a storage device, such as database 250 with measurement results for these and/or other parameters indicative of patient health. The resulting database may further include patient health outcomes that further help to evaluate the effect of different ranges for the identified parameters. For example, the diagnostic system may be configured to determine threshold ranges for a given patient for each parameter.

The disclosed diagnostic system may be configured to perform one or more processes to apply a diagnostic test to patient data collected during an FMD process. For example, a diagnostic tool may be configured to determine values for one or more parameters, such as sensitivity, resistance, and integrity, based on the FMD test. The diagnostic tool may be further configured to determine one or more thresholds for identifying patient health based on patient-specific information. The diagnostic tool may be configured to compare the determined parameter values to the thresholds to determine an output indicative of a patient health. The diagnostic tool may be configured to provide the output to a user (e.g., a medical practitioner) for use in a patient diagnosis or evaluation. The diagnostic tool may also be configured to use the medical outcome of the patient to further refine the underlying algorithms and databases for determining parameters and thresholds.

Although embodiments have been described in terms of exemplary features, they are not limited thereto. Rather, the appended claims should be construed broadly, to include other variants and embodiments, which may be made by those skilled in the art without departing from the scope and range of equivalents.

What is claimed is:

1. A diagnostic system comprising:
a measurement tool configured to collect image data of an artery subject to a flow-mediated dilation (FMD) test; and
a diagnostic tool comprising:
a communications interface;
a memory storing instructions; and
at least one processor coupled to the communications interface and to the memory, the at least one processor being configured to execute the instructions to perform operations comprising:
receiving measurement data comprising a change in diameter of the artery subject to the FMD test over time from an initiation of the FMD test through the artery's substantial recovery to baseline, the measurement data derived from the image data;
determining an FMD parameter value by applying a finite difference model to the received measurement data, wherein the FMD parameter value comprises one or more of a sensitivity of the artery to softening in response to a changing wall shear stress (WSS), resistance of the artery to softening in response to a changing WSS, and integrity of mechanotransduction of a tissue-softening signal throughout the artery, each parameter value being associated with an arterial wall subject to the FMD test;
establishing a diagnostic threshold based on patient medical information;
determining a diagnostic result of the FMD test by comparing the FMD parameter value to the diagnostic threshold; and providing the diagnostic result of the FMD test through an output module of the diagnostic apparatus.

2. The diagnostic system of claim 1, wherein the FMD parameter value comprises a patient-specific measurement resulting from the FMD test.

3. The diagnostic system of claim 1, further comprising a data analysis tool configured to receive the image data and derive the measurement data from the received image data.

4. The diagnostic system of claim 1, wherein the measurement tool comprises an ultrasound imaging device.

5. The diagnostic system of claim 1, wherein the diagnostic threshold comprises a static threshold or a dynamic threshold.

6. The diagnostic system of claim 1, wherein the patient information corresponds to at least one of age, family medical history, smoking history, and sex.

7. The diagnostic system of claim 1, wherein the at least one processor is further configured to execute the instructions to perform operations comprising:
retrieving medical history of a patient of the FMD test; and
determining the FMD parameter value based on the medical history and measurement data.

8. The diagnostic system of claim 1, wherein the FMD test is a brachial artery flow-mediated dilation test.

9. The diagnostic system of claim 1, wherein the diagnostic threshold comprises a range of thresholds corresponding to the patient medical information, and wherein providing the diagnostic result through the output module further comprises presenting a graphical representation of the range of thresholds and a marker denoting the diagnostic result, the marker being presented within the graphical representation in relation to the range of thresholds.

10. The diagnostic system of claim 1, wherein the diagnostic result comprises a prediction in a physical status of a patient of the respective FMD test.

11. The diagnostic system of claim 1, wherein the at least one processor is further configured to execute the instructions to perform operations comprising:
applying at least one of a machine learning processing or neural network processing to adjust one or more algorithms used to determine the FMD parameter value and the diagnostic threshold from the measurement data.

12. The diagnostic system of claim 1, wherein the sensitivity of the artery to softening in response to a changing wall shear stress is $$E_{min}^* = \frac{E_\infty}{E_0},$$

the resistance of the artery to softening in response to a changing WSS is $B = \beta s_0$, and the integrity of mechanotransduction of a tissue-softening signal throughout the artery is $$\gamma = \frac{a_s}{r_{in}^2 \xi}$$

where $E_\infty$ is the modulus of elasticity of an artery wall for a shear stress approaching infinity, $E_0$ is the modulus of elasticity of the artery wall for a shear stress of zero, β is a property indicative of the artery wall's resistance to a changing shear stress, $$s_0 = \frac{4\mu q}{\pi r_{in}^3},$$

where μ is the dynamic viscosity of the blood within the artery, q is the blood flow rate, $a_s$ is diffusivity, $r_{in}$ is the inner radius of the artery, and ξ is a property indicative of the artery's responsiveness to a changing sheer stress.

13. The diagnostic system of claim 12, wherein the at least one processor is further configured to execute the instructions to perform operations comprising:

determining a plurality of FMD parameter values based on the received measurement data, wherein the FMD parameter values comprise each of $$E_{min}^*, B, \text{ and } \gamma,$$

14. A method comprising:

collecting image data of an artery subject to a flow-mediated dilation (FMD) test;

deriving measurement data from the image data, wherein the measurement data comprises a change in diameter of the artery subject to the FMD test over time from an initiation of the FMD test through the artery's substantial recovery to baseline;

determining an FMD parameter value by applying a finite difference model to the measurement data, wherein the FMD parameter value comprises one or more of a sensitivity of the artery to softening in response to a changing wall shear stress (WSS), resistance of the artery to softening in response to a changing WSS, and integrity of mechanotransduction of a tissue-softening signal throughout the artery, each parameter value being associated with an arterial wall subject to the FMD test;

establishing a diagnostic threshold based on patient medical information;

determining a diagnostic result of the FMD test by comparing the FMD parameter value to the diagnostic threshold; and providing the diagnostic result of the FMD test through an output module of a diagnostic apparatus.

15. The computer-implemented method of claim 14, wherein the FMD parameter value comprises a patient-specific measurement resulting from the FMD test.

16. The computer-implemented method of claim 14, wherein the diagnostic threshold comprises a static threshold or a dynamic threshold.

17. The computer-implemented method of claim 14, further comprising:

retrieving medical history of a patient of the FMD test; and determining the FMD parameter value based on the medical history and measurement data.

18. The computer-implemented method of claim 14, further comprising applying at least one of a machine learning process or neural network processing to adjust one or more algorithms used to determine the FMD parameter value and the diagnostic threshold from the measurement data.

19. A tangible, non-transitory computer-readable medium storing instructions that, when executed by at least one processor, cause the at least one processor to perform a method, comprising:

collecting image data of an artery subject to a flow-mediated dilation (FMD) test;

deriving measurement data from the image data, wherein the measurement data comprises a change in diameter of the artery subject to the FMD test over time from an initiation of the FMD test through the artery's substantial recovery to baseline;

determining an FMD parameter value by applying a finite difference model to the measurement data wherein, the FMD parameter value comprises one or more of a sensitivity of the artery to softening in response to a changing wall shear stress (WSS), resistance of the artery to softening in response to a changing WSS, and integrity of mechanotransduction of a tissue-softening signal throughout the artery, each parameter value being associated with an arterial wall subject to the FMD test;

establishing a diagnostic threshold based on patient medical information;

determining a diagnostic result of the FMD test by comparing the FMD parameter value to the diagnostic threshold; and providing the diagnostic result of the FMD test through an output module of a diagnostic apparatus.

20. The tangible, non-transitory computer-readable medium of claim 19, containing further stored instructions that, when executed by at least one processor, cause the at least one processor to further perform:

applying at least one of a machine learning process or neural network processing to adjust one or more algorithms used to determine the FMD parameter value and the diagnostic threshold from the measurement data.

* * * * *